(12) United States Patent
Hunziker et al.

(10) Patent No.: US 10,669,285 B2
(45) Date of Patent: Jun. 2, 2020

(54) CONDENSED [1,4] DIAZEPINE COMPOUNDS AS AUTOTAXIN (ATX) AND LYSOPHOSPHATIDIC ACID (LPA) PRODUCTION INHIBITORS

(71) Applicant: Hoffmann-La Roche Inc., Little Falls, NJ (US)

(72) Inventors: Daniel Hunziker, Moehlin (CH); Jerome Hert, Basel (CH); Holger Kuehne, Loerrach (DE); Patrizio Mattei, Riehen (CH); Markus Rudolph, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/272,085

(22) Filed: Sep. 21, 2016

(65) Prior Publication Data

US 2017/0008913 A1    Jan. 12, 2017

Related U.S. Application Data

(63) Continuation of application No. PCT/EP2015/056041, filed on Mar. 23, 2015.

(30) Foreign Application Priority Data

Mar. 26, 2014 (EP) .................................... 14161756

(51) Int. Cl.
*C07D 519/00* (2006.01)
*C07D 487/04* (2006.01)

(52) U.S. Cl.
CPC ......... *C07D 519/00* (2013.01); *C07D 487/04* (2013.01)

(58) Field of Classification Search
CPC .............................. C07D 519/00; C07D 487/04
See application file for complete search history.

(56) References Cited

U.S. PATENT DOCUMENTS

| | | | |
|---|---|---|---|
| 3,392,149 A | 7/1968 | von der Emden et al. |
| 5,202,322 A | 4/1993 | Allen et al. |
| 5,238,942 A | 8/1993 | Chakravarty et al. |
| 5,240,928 A | 8/1993 | Allen et al. |
| 5,290,780 A | 3/1994 | Venkatesan et al. |
| 5,304,565 A | 4/1994 | Morimoto et al. |
| 5,358,951 A | 10/1994 | Levin et al. |
| 5,472,961 A | 5/1995 | Gottschlich et al. |
| 5,470,975 A | 11/1995 | Atwai |
| 5,532,243 A | 7/1996 | Gilligan |
| 6,821,964 B2 | 11/2004 | Colon-Cruz et al. |
| 6,841,560 B2 | 1/2005 | Thompson et al. |
| 8,329,907 B2 | 12/2012 | Schultz et al. |
| 8,697,883 B2 | 4/2014 | Abouabdellah et al. |
| 8,841,324 B2 | 9/2014 | Staehle et al. |
| 9,029,387 B2 | 5/2015 | Staehle et al. |
| 9,493,486 B2 | 11/2016 | Hunziker et al. |
| 9,802,944 B2 | 10/2017 | Di Giorgio et al. |
| 10,208,052 B1 | 2/2019 | Zheng et al. |
| 2005/0203112 A1 | 9/2005 | Castonguay et al. |
| 2008/0090802 A1 | 4/2008 | Letourneau et al. |
| 2010/0222341 A1 | 9/2010 | Schiemann et al. |
| 2010/0298290 A1 | 11/2010 | Anand et al. |
| 2011/0230471 A1 | 9/2011 | Staehle et al. |
| 2012/0015959 A1 | 1/2012 | Staehle et al. |
| 2012/0095040 A1 | 4/2012 | Abouabdellah et al. |
| 2012/0115852 A1 | 5/2012 | Schultz et al. |
| 2012/0115858 A1 | 5/2012 | Tesconi et al. |
| 2015/0353559 A1 | 12/2015 | Hert et al. |
| 2015/0376194 A1 | 12/2015 | Hert et al. |
| 2016/0264586 A1 | 9/2016 | Mattei et al. |
| 2017/0008900 A1 | 1/2017 | Di Giorgio et al. |
| 2017/0008913 A1 | 1/2017 | Hunziker et al. |
| 2017/0029425 A1 | 2/2017 | Hunziker et al. |
| 2017/0050960 A1 | 2/2017 | Hert et al. |

FOREIGN PATENT DOCUMENTS

| CA | 2 768 095 | | 1/2011 |
|---|---|---|---|
| CA | 2878442 | A1 | 4/2014 |
| CN | 1751047 | A1 | 3/2006 |
| CN | 102459207 | A | 5/2012 |

(Continued)

OTHER PUBLICATIONS 1206969-43-8,Database Registry [retrieved online May 25, 2016] Chemical Abstracts Service, Feb. 22, 2010 (Feb. 22, 2010), BroadPharm:XP002707619, retrieved from STN Database accession No. 1206969-43-8 the whole document.
959567-58-9,Database Registry [retrieved May 25, 2016] Chemical Abstracts Service Dec. 26, 2007 (Dec. 26, 2007), NIH Chemical Genomics Center: XP002707620, retrieved from STN Database accession No. 959567-58-9.
Albers et al., "Chemical Evolution of Autotaxin Hinhibitors" Chem Rev 112(5):2593-2603 (May 9, 2012).
Albers et al., "Chemical Evolution of Autotaxin Inhibitors" Chemical Reviews (XP055073234), 112(5):2593-2603 (May 9, 2012).
Barbayianni et al., "Autotaxin inhibitors: a patent review" Expert Opin Ther Patents 23(9):1123-1132 (2013).
Benesh et al., Febs Lett 588:2712-2727 (2014).
CAS Registry Database, 1300725-30-7,Database Registry [retrieved online May 25, 2016] Chemical Abstracts Service May 25, 2011 (May 25, 2011), Focus Synthesis LLC: XP002707618, retrieved from STN Database accession No. 1300725-30-7 the whole document.

(Continued)

*Primary Examiner* — Angela C Brown-Pettigrew
(74) *Attorney, Agent, or Firm* — Katherine J. Mackenzie

(57) ABSTRACT

Compounds of formula (I)

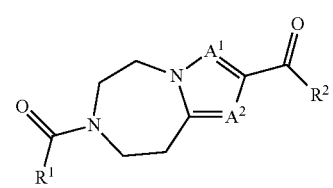

wherein $R^1$, $R^2$, $A^1$ and $A^2$ are as described herein, compositions including the compounds and methods of using the compounds as autotaxin inhibitors.

26 Claims, No Drawings

(56) References Cited

FOREIGN PATENT DOCUMENTS

| | | |
|---|---|---|
| EP | 0 417 631 A2 | 3/1991 |
| EP | 0417631 A2 | 3/1991 |
| EP | 2 301 936 A1 | 3/2011 |
| EP | 2301936 A1 | 3/2011 |
| EP | 3385261 A1 | 10/2018 |
| JP | 2001039950 | 2/2001 |
| JP | 2008-31064 | 2/2008 |
| JP | 2008-31064 A | 2/2008 |
| JP | 2008-501743 | 2/2008 |
| JP | 2008-540547 | 11/2008 |
| JP | 2009-161449 | 7/2009 |
| JP | 2011-502150 | 1/2011 |
| RU | 2 375 352 C2 | 12/2009 |
| WO | 99/40070 | 8/1999 |
| WO | 01/30780 | 5/2001 |
| WO | 02/070523 | 9/2002 |
| WO | 02/070523 A1 | 9/2002 |
| WO | 2004/074291 | 9/2004 |
| WO | 2004/074291 A1 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | WO2008116881 * | 10/2008 ........... C07D 401/06 |
| WO | 2008/135141 A1 | 11/2008 |
| WO | 2009/046841 A2 | 4/2009 |
| WO | 2009/054914 A1 | 4/2009 |
| WO | 2009/058347 | 5/2009 |
| WO | 2009/154132 | 12/2009 |
| WO | 2010/115491 | 1/2010 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108651 | 9/2010 |
| WO | 2010/112116 A1 | 10/2010 |
| WO | 2010/112124 | 10/2010 |
| WO | 2010/112124 A1 | 10/2010 |
| WO | 2010/115491 A2 | 10/2010 |
| WO | 2010/130944 | 11/2010 |
| WO | 2010/130944 A1 | 11/2010 |
| WO | 2010/135524 | 11/2010 |
| WO | 2010/141817 A1 | 12/2010 |
| WO | 2011/006569 | 1/2011 |
| WO | 2011/006569 A1 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 | 9/2011 |
| WO | 2011/141716 A2 | 11/2011 |
| WO | 2009/154132 | 12/2011 |
| WO | 2011/151461 A2 | 12/2011 |
| WO | 2012/020008 | 2/2012 |
| WO | 2012/024620 | 2/2012 |
| WO | 2012/028243 | 3/2012 |
| WO | 2012/080727 | 6/2012 |
| WO | 2012/166415 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2013/186159 | 12/2013 |
| WO | 2014/007951 | 1/2014 |
| WO | 2014/018881 | 1/2014 |
| WO | 2014/018891 | 1/2014 |
| WO | 2014/048865 | 4/2014 |
| WO | 2014/048881 | 4/2014 |
| WO | 2014/055548 | 4/2014 |
| WO | 2014/066659 | 5/2014 |
| WO | 2014/133112 A1 | 9/2014 |
| WO | 2014/139324 | 9/2014 |
| WO | 2014/139978 | 9/2014 |
| WO | 2014/139978 A1 | 9/2014 |
| WO | 2014/143579 | 9/2014 |
| WO | 2014/152725 A1 | 9/2014 |
| WO | 2014/164905 | 10/2014 |
| WO | 2015/008230 A1 | 1/2015 |
| WO | 2015/058031 | 4/2015 |
| WO | 2015/077503 | 5/2015 |
| WO | 2015/078800 A1 | 6/2015 |
| WO | 2015/078803 | 6/2015 |
| WO | 2015/144480 | 10/2015 |
| WO | 2015/144605 A1 | 10/2015 |
| WO | 2015/144609 | 10/2015 |
| WO | 2015/144803 | 10/2015 |
| WO | 2015/154023 A1 | 10/2015 |
| WO | 2016/061160 | 4/2016 |
| WO | 2016/128529 A1 | 8/2016 |
| WO | 2016/162390 | 10/2016 |
| WO | 2017/005073 | 1/2017 |
| WO | 2017/037146 | 3/2017 |
| WO | 2017/037670 A1 | 3/2017 |
| WO | 2017/050732 | 3/2017 |
| WO | 2017/050747 | 3/2017 |
| WO | 2017/050791 | 3/2017 |
| WO | 2017/050791 A1 | 3/2017 |
| WO | 2017/050792 | 3/2017 |
| WO | 2017/053722 A1 | 3/2017 |
| WO | 2017/091673 A2 | 6/2017 |
| WO | 2017/139978 | 8/2017 |
| WO | 2018/167001 A1 | 9/2018 |
| WO | 2018/167113 | 9/2018 |

OTHER PUBLICATIONS

CAS Registry Database, 1352926-14-7,Database Registry [retrieved online May 25, 2016] Chemical Abstracts Service Jan. 12, 2012 (Jan. 12, 2012) All i chern LLC: XP002707617, retrieved from STN Database accession No. 1352926-14-7 see also RN: 135295-74-6; the whole document.

Database Capulus (online) Chemical Abstracts Service Columbus Ohio, 1993, Database accession No. 1994:483155 RN156411-73-3, 156411-74-4 (1993).

Garcia-Gutierrez et al., "Novel inhibitors to Taenia solium Cu/Zn superoxide dismutase identified by virtual screening" J. Computer. Aided Molecular Design 25:1135-1145 (2011).

Gierse et al., Pharmacol Exp Ther 334:310-317 (2010).

Harald M.H.G. Albers et al., "Discovery and Optimization of Boronic Acid Based Inhibitors of Autotaxin" Journal of Medicinal Chemistry 53(13):4958-4967 (Jul. 8, 2010).

International Search Report for International Patent Application No. PCT/EP2014/075360.

ISR for PCT/EP2013/061890.

ISR for PCT/EP2013/069679.

Jones et al., ACS Med Chem Lett 7:857-861 ( 2016).

Kung et al., "Identification of spirocyclic piperidine-azetidine inverse agonists of the ghrelin receptor" Bioorganic & Medicinal Chemistry Letters (XP028490993), 22(13):4281-4287 (May 8, 2012).

(56) References Cited

OTHER PUBLICATIONS

Litherland et al., "The Amino-derivatives of Pentuerythritol. Part I. Perparation." (Published on Jan. 1, 1938. Downloaded by Roche Group on May 24, 2016 17:23:15.),:1588-1595.
Mayo Clinic Staff, (Lupus[online], retrieved from the internet on Jan. 24, 2017; http://www.mayoclinic.org/diseases-conditions/lupus basics/definition/CON-20019676) 2017.
Orr et al., "One-pot synthesis of chiral azetidines from chloroaldehyde and chiral amines" Tetrahedron Letters (XP055073241), 52:3618-3620 ( 2011).
Overberger et al., "Absolute Configuration of 2, 7-Diazaspiro[4. 4Inonane. A Reassignment" J. Org. Chem. (XP055072840), 46:2757-2764 ( 1981).
Sippy et al., "Preparation and characterization of N-(3-pyridinyl) spirocyclic diamines as ligands for nicotinic acetylcholine receptors" Bioorganic & Medicinal Chemistry Letters 19:1682-1685 ( 2009).
Stocks et al., "A Practical Method for Targeted Library Design Balancing Lead-like Properties with Diversity" Chem Med Chem (XP002707616), 4:800-808 (2009).
Written Opinion for PCT/EP2013/061890.
Written Opinion for PCT/EP2013/069679.
pgs. 1-13 (STN Columbus (STN International) Oct. 9, 2015).
Database Registry Numbers, Chemical Abstract Service (CAS), 38 pages (Dec. 26, 2007).
Harald M.H.G. Albers et al., "Structure-Based Design of Novel Boronic Acid-Based Inhibitors of Autotaxin" Journal of Medicinal Chemistry 54(13):4619-4626 ( 2011).
Patani et al., "Bioisosterism: A Rational Approach in Drug Design," Chem.Ref. (1996), vol. 96, pp. 3147-3176.
Sheridan et al., "The Most Common Chemical Replacements in Drug-Like Compounds" J. Chem. Inf. Comput. Sci. 42(1):103-108 ( 2002).
Albers et al., "Discovery and Optimization of Boronic Acid Based Inhibitors of Autotaxin" Journal of Medicinal Chemistry 53(13):4958-4967 (Jul. 8, 2010).
Anderson, "The Process of Structure-Based Drug Design"Chemistry & Biology 10:787-797 (Sep. 2003).
Angeli et al., "Synthesis and carbonic anhydrase inhibition of polycyclic imides moieties" Bioorganic & Medicinal Chemistry 25(20):5373-5379 (Oct. 20, 2017).
Armstrong, J ., et al., "Purification and Properties of Human Erythrocyte Carbonic Anhydrases" J Biol Chem 241(21):5137-5149 (Nov. 10, 1966).
Bora, Rajesh O., et al, "[1, 2, 4] Oxadiazoles: Synthesis and Biological Applications" Mini-Reviews in Med. Chem 14(4):355-369 (Mar. 13, 2014).
CAS Database Registry, ID#1206969-43-8 [retrieved online May 25, 2016], Feb. 22, 2010 (Feb. 22, 2010), BroadPharm, retrieved from STN Database accession No. 1206969-43-8 the whole document.
Erdik, Ender, "Transition Metal Catalyzed Reactions of Organozinc Reagents" Tetrahedron Report No. 23 48(44):9577-9648 (Jan. 1, 1992).
Farina, V. et al. Organic Reactions "The Stille Reaction" Paquette, Leo A., New York-US:Wiley and Sons, Vol. 50:1-704 (Apr. 1, 1997).
Garcia-Gutierrez et al., "Novel inhibitors to Taenia solium Cu/Zn superoxide dismutase identifed by virtual screening" J. Computer. Aided Molecular Design 25:1135-1145 ( 2011).
Gierse et al., "A Novel Autotaxin Inhibitor Reduces Lysophosphatidic Acid Levels in Plasma and the Site of Inflammation" Pharmacol Exp Ther 334:310-317 ( 2010).
Green et al. Protective Groups in Organic Synthesis (Table of Contents only, in 4 pages), Second edition, New York:John Wiley & Sons, Inc., ( 1991).
Hall, Dennis. ed. et al. Boronic Acids: Preparation, Applications in Organic Synthesis and Medicine (Description and table of contents only, 2 pages), Hall, Dennis,Wiley,: 1-571 (Jan. 1, 2006).

Hemming, K. Science of Synthesis, Product 13: 1, 2, 3-Triazoles "Product Class 6: 1,2,4-Oxadiazoles" Storr, R.C. & Gilchrist, T.L., eds., Stuttgart-DE:Thieme Verlagsgruppe, Vol. 13:127-184 (Jan. 1, 2004).
Henke, Brad R., et al., "Optimization of 3-(1H-Indazol-3 -y1methy1)-1,5-benzodiazepines as Potent, Orally Active CCK-A Agonists" J Med Chem 40:2706-2725 (Apr. 22, 1997).
Hoeglund et al., "Optimization of a pidemidic acid autotaxin inhibitor" Journal of Medicinal Chemistry 53:1056-1066 (Dec. 30, 2009).
"International Preliminary Report on Patentability—PCT/EP2018/056140": pp. 1-8 (Sep. 26, 2019).
"International Search Report—PCT/EP2014/054631": pp. 1-4 (Apr. 15, 2014).
"International Search Report—PCT/EP2015/056041":pp. 1-5 (May 6, 2015).
"International Search Report—PCT/EP2016/072277",:pp. 1-5 (Dec. 8, 2016).
"International Search Report—PCT/EP2016/072349":pp. 1-5 (Nov. 29, 2016).
"International Search Report—PCT/EP2018/056140":pp. 1-9 (May 4, 2018).
"International Search Report—PCT/EP2018/056324",:pp. 1-7 (May 8, 2018).
"International Search Report—PCT/EP2015/056032",:pp. 1-5 (Apr. 23, 2015).
"International Search Report—PCT/EP2016/057549":pp. 1-5 (Jun. 22, 2016).
"International Search Report—PCT/EP2016/072243":pp. 1-5 (Dec. 6, 2016).
"International Search Report—PCT/EP2016/072347":pp. 1-5 (Jan. 17, 2017).
"International Search Report—PCT/EP2016/070561":pp. 1-6 (Oct. 28, 2016).
Li, Jie Jack et al. Name Reactions for Homologation, Part 1 "Name Reactions for Homologation, Part 1" (Abstract of text, author information, and table of contents only, 2 pages),Wiley and Sons,:1-685 (May 1, 2009).
Matralis et al., "Development and therapeutic potential of autotaxin small molecule inhibitors: From bench to advanced clinical trials" Med. Res. Rev.:1-38 ( 2018).
Mitchell, Terence N., "Palladium-Catalysed Reactions of Organotin Compounds" Synthesis 9:803-815 (Aug. 16, 1991).
Negishi, Ei-ichi, et al. Metal-Catalyzed Cross-Coupling Reactions "Chapter 1. Palladium or NickelCatalyzed CrossCoupling with Organometals Containing Zinc, Magnesium, Aluminum, and Zirconium" (Preface, table of contents, list of contributors only, 22 pages), Diederich, Francois, Stang, Peter J., Weinheim, DE:Wiley-VCH Verlag GmbH,:1-47 (Jan. 1, 2004).
Polshettiwar, Vivek, et al., "Suzuki-Miyaura Cross-Coupling Reactions in Aqueous Media: Green and Sustainable Syntheses of Biaryls" ChemSUSChem 3:502-522 (Jan. 1, 2010).
Pouliot, Marie-France, et al., "Synthesis of 1,3,4-oxadiazoles from 1,2-diacylhydrazines using [Et2NSF2]BF4 as a practical cyclodehydration agent" Org. Biomol. Chem 10:988-993 (Oct. 27, 2012).
Schlaeger, E. et al., "The protein hydrolysate, primatone RL, is a cost-effective multiple growth promoter of mammalian cel culture in serum-containing and serum-free medi and displays anti-apoptosis properties" J. of Immunological Methods 194:191-199 (1996).
Sheridan et al., "Cautious optimism surrounds early clinical data for PD-1 blocker" Nature Biotechnology 30:729-730 (2012).
Stille, John K., "The Palladium-Catalyzed Cross-Coupling Reactions of Organotin Reagents with Organic Electrophiles" Angew Chem. Int. Ed. Engl. 25:508-524 (Jan. 1, 1986).
Suzuki, A., et al., "Palladium-Catalyzed Cross-Coupling Reactions of Organoboron Compounds" Chem Rev. 95:2457-2483 (Jan. 31, 1995).
Suzuki, A., et al., "Recent advances in the cross-coupling reactions of organoboron derivatives with organic electrophiles, 1995-1998" J Organomet Chem 576:147-168 (Jan. 1, 1999).

(56) References Cited

OTHER PUBLICATIONS

Suzuki, A., et al., "Synthetic Studies via the cross-coupling reaction of organoboron derivatives with organic halides" Pure Appl Chem 63(3):419-422 (Jan. 1, 1991).
Thiel, "Structure-aided drug design's next generaton" Nature Biotechnology 22(5):513-519 ( 2004).
Tucker, Thomas J., et al., "Discovery of 3-{5-[(6-Amino-1H-pyrazolo [3,4-b]pyridine-3-yl)methoxy]2-chlorophenoxy}-5-chlorobenzonitrile (MK-4965): A Potent, Orally Bioavailable HIV-1 Non-Nucleoside Reverse Transcriptase Inhibitor with Improved Potency against Key Mutant Viruses" J Med Chem 51:6503-6511 (Jul. 11, 2008).
WO:ISR, pp. 1-6 (International Search Report from PCT/EP2016/070561 dated Oct. 23, 2016, Oct. 12, 2016).

\* cited by examiner

CONDENSED [1,4] DIAZEPINE COMPOUNDS AS AUTOTAXIN (ATX) AND LYSOPHOSPHATIDIC ACID (LPA) PRODUCTION INHIBITORS

CROSS-REFERENCE TO RELATED APPLICATIONS

This Application is a continuation of PCT/EP2015/056041 filed on Mar. 23, 2015, which claims priority to EP 14161756.3 filed on Mar. 26, 2014, the disclosures of which are incorporated herein by reference.

BACKGROUND OF THE INVENTION

Autotaxin (ATX) is a secreted enzyme also called ecto-nucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1 (vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

SUMMARY OF THE INVENTION

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

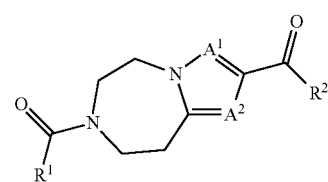

wherein $R^1$ is alkyl, haloalkyl, substituted cycloalkyl, substituted cycloalkylalkyl, substituted phenyl, substituted phenylalkyl, substituted phenoxyalkyl, substituted phenylalkoxy, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl or substituted benzofuran-2-yl, wherein substituted cycloalkyl, substituted cycloalkylalkyl, substituted phenyl, substituted phenylalkyl, substituted phenoxyalkyl, substituted phenylalkoxy, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl and substituted benzofuran-2-yl are substituted with $R^3$, $R^4$ and $R^5$;

$A^1$ is —N— or —$CR^7$—;

$A^2$ is —N— or —$CR^8$— and at least one of $A^1$ and $A^2$ is —N—;

$R^2$ is selected from the ring systems A, B, C, D, E, F, G, H, I, K and L.

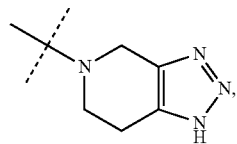

A

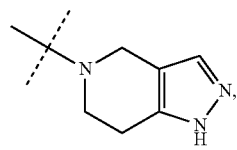

B

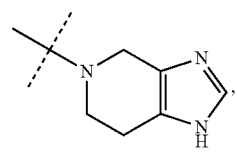

C

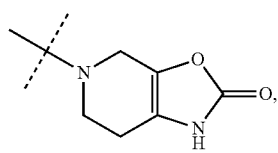

D

-continued

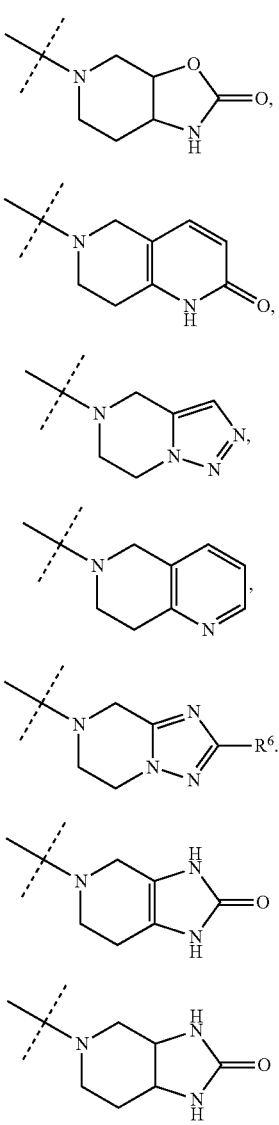

$R^3$, $R^4$ and $R^5$ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, heterocycloalkylalkoxy, phenyl, substituted phenyl, pyridinyl, substituted pyridinyl, halogen, hydroxy, cyano, alkylsulfanyl, haloalkylsulfanyl, cycloalkylsulfanyl, alkylsulfinyl, haloalkylsulfinyl, cycloalkylsulfinyl, alkyl sulfonyl, haloalkylsulfonyl, cycloalkylsulfonyl, alkylcarbonylamino, substituted aminosulfonyl, substituted amino and substituted aminoalkyl, wherein substituted aminosulfonyl, substituted amino and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl, and wherein substituted phenyl and substituted pyridinyl are optionally substituted with one to three substituents independently selected from alkyl, halogen, haloalkyl, alkoxy and haloalkoxy;

$R^6$ is H, alkyl, haloalkyl or cycloalkyl;
$R^7$ and $R^8$ are independently selected from H, alkyl, haloalkyl or cycloalkyl;
or pharmaceutically acceptable salts.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and -chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

DETAILED DESCRIPTION OF THE INVENTION

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include isopropoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group include methoxymethyl, methoxyethyl and isopropoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy or ethoxy. Particular alkoxycarbonyl group include groups of the formula —C(O)—R', wherein R' is methoxy.

The term "alkoxyhaloalkyl" denotes a haloalkyl group wherein at least one of the hydrogen atoms of the haloalkyl group has been replaced by an alkoxy group. Exemplary alkoxyalkyl groups include methoxytrifluoroethyl, ethoxytrifluoroethyl, methoxytrifluoropropyl and ethoxytrifluoropropyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, tert-butyl and pentyl. Particular alkyl groups include methyl, ethyl, propyl and isopropyl. More particular alkyl groups are ethyl and isopropyl.

The term "alkylcarbonyl" denotes a group of the formula —C(O)—R', wherein R' is an alkyl group. Examples of alkylcarbonyl groups include groups of the formula —C(O)—R', wherein R' is methyl or ethyl. Particular alkylcarbonyl groups include groups of the formula —C(O)—R', wherein R' is methyl.

The term "alkylcarbonylamino" denotes a group of the formula —NH—C(O)—R', wherein R' is an alkyl group. Examples of alkylcarbonylamino groups include groups of the formula —NH—C(O)—R', wherein R' is methyl, ethyl, propyl, isopropyl, n-butyl, iso-butyl, sec-butyl, tert-butyl or pentyl. Particular alkylcarbonylamino group include group of the formula —NH—C(O)—R', wherein R' is tert-butyl.

The term "alkylsulfanyl" denotes a group of the formula —S—R', wherein R' is an alkyl group. Examples of alkylsulfanyl groups include groups of the formula —S—R', wherein R' is methyl, ethyl, n-propyl, isopropyl, n-butyl, isobutyl or tert-butyl. Particular alkylsulfanyl groups include group of the formula —S—R', wherein R' is methyl.

The term "alkylsulfinyl" denotes a group of the formula —S(O)—R', wherein R' is an alkyl group. Examples of alkylsulfinyl groups include groups of the formula —S(O)—R', wherein R' is methyl, ethyl, n-propyl, n-butyl, isobutyl or tert-butyl. Particular alkylsulfinyl groups include group of the formula —S(O)—R', wherein R' is methyl.

The term "alkylsulfonyl" denotes a group of the formula —S(O)$_2$—R', wherein R' is an alkyl group. Examples of alkyl sulfonyl groups include groups of the formula —S(O)$_2$—R', wherein R' is methyl, ethyl, n-propyl, isopropyl, n-butyl, isobutyl or tert-butyl. Particular alkylsulfonyl groups include group of the formula —S(O)$_2$—R', wherein R' is methyl.

The term "alkylsulfonylamino" denotes a group of the formula —NH—S(O)$_2$—R', wherein R' is an alkyl group. Examples of alkylsulfonylamino groups include groups of the formula —NH—S(O)$_2$—R', wherein R' is methyl or ethyl. Particular a alkylsulfonylamino groups include groups of the formula —NH—S(O)$_2$—R', wherein R' is methyl.

The term "amino" denotes a —NH$_2$ group.

The term "aminoalkyl" denotes an alkyl group wherein at least one of the hydrogen atoms of the alkyl group has been replaced by an aminogroup. Examples of aminoalkyl include aminomethyl, aminoethyl, amino-1-methyl-ethyl, aminopropyl, aminomethylpropyl and aminopropyl. Particular examples are aminomethyl and haminoethyl.

The term "aminosulfonyl" denotes a —S(O)$_2$—NH$_2$ group.

The term "carbonyl" denotes a —C(O)— group.

The term "carboxy" denotes a —COOH group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl groups include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamentanylmethyl and adamantanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamantanylmethyl and adamantanylethyl. Further particular examples cycloalkylalkyl are cyclohexylmethyl, cyclohexylethyl, bicyclo[4.1.0]heptanylmethyl, bicyclo[2.2.2]octanylmethyl, adamantanylmethyl and adamantanyl ethyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "cycloalkylsulfanyl" denotes a group of the formula —S—R', wherein R' is a cycloalkyl group. Examples of cycloalkylsulfanyl groups include groups of the formula —S—R', wherein R' is cyclopropyl.

The term "cycloalkylsulfinyl" denotes a group of the formula —S(O)—R', wherein R' is a cycloalkyl group. Examples of cycloalkylsulfinyl groups include groups of the formula —S(O)—R', wherein R' is cyclopropyl.

The term "cycloalkylsulfonyl" denotes a group of the formula —S(O)$_2$—R', wherein R' is a cycloalkyl group. Examples of cycloalkylsulfonyl groups include groups of the formula —S(O)$_2$—R', wherein R' is cyclopropyl.

The term "haloalkoxy" denotes an alkoxy group wherein at least one of the hydrogen atoms of the alkoxy group has been replaced by the same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy group is trifluoromethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "haloalkylsulfanyl" denotes a group of the formula —S—R', wherein R' is a haloalkyl group. Examples of haloalkylsulfanyl groups include groups of the formula —S—R', wherein R' is trifluoromethyl.

The term "haloalkylsulfinyl" denotes a group of the formula —S(O)—R', wherein R' is a haloalkyl group. Examples of haloalkylsulfinyl groups include groups of the formula —S(O)—R', wherein R' is trifluoromethyl.

The term "haloalkylsulfonyl" denotes a group of the formula —S(O)$_2$—R', wherein R' is a haloalkyl group.

Examples of haloalkylsulfonyl groups include groups of the formula —S(O)$_2$—R', wherein R' is trifluoromethyl.

The term "halogen" and "halo" are used interchangeably herein and denote fluoro, chloro, bromo, or iodo. Particular halogen is fluoro.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl. Particular example of heterocycloalkyl groups is tetrahydropyranyl.

The term "heterocycloalkylalkoxy" denotes an alkoxy group wherein at least one of the hydrogen atoms of the alkoxy group is replaced by a heterocycloalkyl group. Examples of heterocycloalkylalkoxy include tetrahydropyranylmethoxy, tetrahydrofuranylmethoxy, oxetanylmethoxy, tetrahydropyranylethoxy, tetrahydrofuranylethoxy and oxetanylethoxy. Particular heterocycloalkylalkoxy is tetrahydropyranylmethoxy.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methyl-ethyl, hydroxypropyl, hydroxymethylpropyl and dihydroxypropyl. Particular examples are hydroxymethyl and hydroxyethyl.

The term "hydroxyhaloalkyl" denotes a haloalkyl group wherein at least one of the hydrogen atoms of the haloalkyl group has been replaced by an hydroxy group. Exemplary hydroxyhaloalkyl groups include hydroxytrifluoroethyl and hydroxytrifluoropropyl. Particular hydroxyhaloalkyl groups include hydroxytrifluoroethyl.

The term "naphthylalkenyl" denotes an alkenyl group wherein at least one of the hydrogen atoms of the alkenyl group has been replaced a naphthynaphthyl. Particular naphthylalkenyl group is naphytylethenyl.

The term "naphthylalkyl" denotes an alkyl group wherein at least one of the hydrogen atoms of the alkyl group has been replaced a naphthyl. Particular naphthylalkyl groups are naphthylmethyl, naphthylethyl and naphthylpropyl.

The term "naphthyloxyalkyl" denotes an alkyl group wherein at least one of the hydrogen atoms of the alkyl group has been replaced by a naphthyloxy group. Exemplary naphthyloxyalkyl groups include naphthyloxymethyl, naphthyloxyethyl and naphthyloxypropyl.

The term "phenoxy" denotes a group of the formula —O—R', wherein R' is a phenyl.

The term "phenoxyalkyl" denotes an alkyl group wherein at least one of the hydrogen atoms of the alkyl group has been replaced by a phenoxy group. Exemplary phenoxyalkyl groups include phenoxymethyl, phenoxyethyl and phenoxypropyl. Particular alkoxyalkyl group is phenoxymethyl.

The term "phenylalkenyl" denotes an alkenyl group wherein at least one of the hydrogen atoms of the alkenyl group has been replaced a phenyl. Particular phenylalkenyl group is phenylethenyl.

The term "phenylalkoxy" denotes an alkoxy group wherein at least one of the hydrogen atoms of the alkoxy group is replaced by a phenyl group. Examples of phenylalkoxy include phenylmethoxy, phenylethoxy and phenylpropoxy. Particular phenylalkoxy is phenylmethoxy.

The term "phenylalkyl" denotes an alkyl group wherein at least one of the hydrogen atoms of the alkyl group has been replaced a phenyl. Particular phenylalkyl groups are benzyl, phenethyl and phenylpropyl. More particular phenylalkyl groups are benzyl and phenethyl. Further particular phenylalkyl group is phenethyl.

The term "phenylalkynyl" denotes an alkynyl group wherein at least one of the hydrogen atoms of the alkynyl group has been replaced a phenyl. Particular phenylalkynyl group is phenylethynyl.

The term "phenylcyloalkyl" denotes a cycloalkyl group wherein at least one of the hydrogen atoms of the cycloalkyl group has been replaced a phenyl. Particular phenylcycloalkyl group is phenylcyclopropyl.

The term "pyridinylalkenyl" denotes an alkenyl group wherein at least one of the hydrogen atoms of the alkenyl group has been replaced a pyridinyl. Particular pyridinylalkenyl group is pyridinylethenyl.

The term "pyridinylalkyl" denotes an alkyl group wherein at least one of the hydrogen atoms of the alkyl group has been replaced a pyridinyl. Particular pyridinylalkyl groups are pyridinylmethyl, pyridinylethyl and pyridinylpropyl. More particular pyridinylalkyl group is pyridinylethyl.

The term "pyridinylalkynyl" denotes an alkynyl group wherein at least one of the hydrogen atoms of the alkynyl group has been replaced a pyridinyl. Particular pyridinylalkynyl group is pyridinylethynyl.

The term "thiophenylalkenyl" denotes an alkenyl group wherein at least one of the hydrogen atoms of the alkenyl group has been replaced a thiophenyl. Particular thiophenylalkenyl group is thiophenylethenyl.

The term "thiophenylalkyl" denotes an alkyl group wherein at least one of the hydrogen atoms of the alkyl group has been replaced a thiophenyl. Particular thiophenylalkyl groups are thiophenylmethyl, thiophenylethyl and thiophenylpropyl. More particular thiophenylalkyl group is thiophenylmethyl.

The term "thiophenylalkynyl" denotes an alkynyl group wherein at least one of the hydrogen atoms of the alkynyl group has been replaced a thiophenyl. Particular thiophenylalkynyl group is thiophenylethynyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz or Z), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein
$R^1$ is alkyl, haloalkyl, substituted cycloalkyl, substituted cycloalkylalkyl, substituted phenyl, substituted phenylalkyl, substituted phenoxyalkyl, substituted phenylalkoxy, substituted phenylcycloalkyl, substituted phenylalkenyl, substituted phenylalkynyl, substituted pyridinyl, substituted pyridinyl alkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl or substituted benzofuran-2-yl, wherein substituted cycloalkyl, substituted cycloalkylalkyl, substituted phenyl, substituted phenyl alkyl, substituted phenoxyalkyl, substituted phenylalkoxy, substituted phenyl cycloalkyl, substituted phenylalkenyl, substituted phenylalkynyl, substituted pyridinyl, substituted pyridinylalkyl, substituted pyridinyl alkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl and substituted benzofuran-2-yl are substituted with $R^3$, $R^4$ and $R^5$;

$A^1$ is —N— or —$CR^7$—;

$A^2$ is —N— or —$CR^8$— and at least one of $A^1$ and $A^2$ is —N—;

$R^2$ is selected from the ring systems A, B, C, D, E, F, G, H, I, K and L.

$R^3$, $R^4$ and $R^5$ are independently selected from H, alkyl, hydroxyalkyl, haloalkyl, hydroxyhaloalkyl, cycloalkyl, cycloalkyl alkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, halogen, hydroxy, cyano, alkylsulfanyl, haloalkylsulfanyl, cycloalkylsulfanyl, alkylsulfinyl, haloalkylsulfinyl, cycloalkylsulfinyl, alkyl sulfonyl, haloalkylsulfonyl, cycloalkylsulfonyl, alkylcarbonylamino, substituted aminosulfonyl, substituted amino and substituted aminoalkyl, wherein substituted aminosulfonyl, substituted amino and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl, and wherein substituted phenyl and substituted pyridinyl are optionally substituted with one to three substituents independently selected from alkyl, halogen, haloalkyl, alkoxy and haloalkoxy;

$R^6$ is H, alkyl, haloalkyl or cycloalkyl;

$R^7$ and $R^8$ are independently selected from H, alkyl, haloalkyl or cycloalkyl;

or pharmaceutically acceptable salts.

Another embodiment of the present invention are compounds according to formula (I) as described herein, wherein $R^1$ is substituted phenylalkyl, substituted phenoxyalkyl or substituted phenylalkoxy, wherein substituted phenylalkyl, substituted phenoxyalkyl and substituted phenylalkoxy are substituted with $R^3$, $R^4$ and $R^5$.

A particular embodiment of the present invention are compounds according to formula (I) as described herein, wherein $R^1$ is substituted phenoxyalkyl or substituted phenylalkoxy, wherein substituted phenoxyalkyl and substituted phenylalkoxy are substituted with $R^3$, $R^4$ and $R^5$.

In a further particular embodiment of the present invention are compounds according to formula (I) as described herein, wherein $R^1$ is phenylalkoxy substituted with $R^3$, $R^4$ and $R^5$.

The present invention also relates to compounds according to formula (I) as described herein, wherein $R^2$ is selected from the ring systems A and O.

A particular embodiment of the present invention are compounds according to formula (I) as described herein, wherein $R^2$ is the ring system A and of formula (Ia).

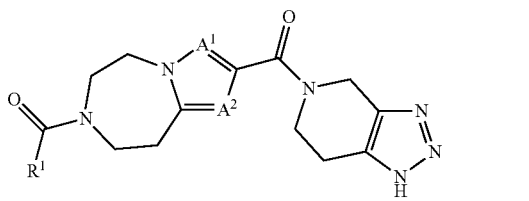

(Ia)

A further embodiment of the present invention are compounds according to formula (I) as described herein, wherein $A^1$ is —N— and $A^2$ is —N— or —$CR^8$—.

Another further embodiment of the present invention are compounds according to formula (I) as described herein, wherein $R^3$, $R^4$ and $R^5$ are independently selected from H, alkyl, cycloalkyl, heterocycloalkylalkoxy, haloalkoxy, halogen, cyano and alkylcarbonylamino.

A particular embodiment of the present invention are compounds according to formula (I) as described herein, wherein $R^3$, $R^4$ and $R^5$ are independently selected from H, alkyl, cycloalkyl, haloalkoxy, halogen, cyano and alkylcarbonylamino.

Another particular embodiment of the present invention are compounds according to formula (I) as described herein, wherein $R^3$ is heterocycloalkylalkoxy, haloalkoxy or cyano.

A further particular embodiment of the present invention are compounds according to formula (I) as described herein, wherein $R^3$ is haloalkoxy or cyano.

Another particular embodiment of the present invention are compounds according to formula (I) as described herein, wherein $R^4$ is H, alkyl, cycloalkyl or halogen.

A further particular embodiment of the present invention are compounds according to formula (I) as described herein, wherein $R^4$ is H, alkyl or halogen.

Also an embodiment of the present invention are compounds according to formula (I) as described herein, wherein $R^5$ is H.

Another embodiment of the present invention are compounds according to formula (I) as described herein, wherein $R^7$ is H.

Another embodiment of the present invention are compounds according to formula (I) as described herein, wherein $R^8$ is H.

A more particular embodiment of the present invention are compounds according to formula (I) as described herein, wherein $R^1$ is substituted phenylalkoxy substituted with $R^3$, $R^4$ and $R^5$;

$A^1$ is —N—;

$A^2$ is —N— or —$CR^8$—;

$R^2$ is the ring system A.

$R^3$ is haloalkoxy or cyano;

$R^4$ is H or halogen;

$R^5$ is H;

$R^8$ is H;

or pharmaceutically acceptable salts.

Particular examples of compounds of formula (I) as described herein are selected from Benzyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

Benzyl 2-(1,4,6,7-tetrahydrotriazolo[4,5-c]pyridine-5-carbonyl)-5,6,8,9-tetrahydroimidazo[1,2-d][1,4]diazepine-7-carboxylate;

[3-Fluoro-4-(trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

2-Fluoro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[4-(Trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

4-Cyanobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-Cyano-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-Cyano-2-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

(4-Cyano-2-propan-2-ylphenyl)methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

[4-Cyano-2-(2,2-dimethylpropanoylamino)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

[4-(Trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[4-Cyano-2-(2,2-dimethylpropanoylamino)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[4-(Trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate;

1-[2-(1,4,6,7-Tetrahydrotriazolo[4,5-c]pyridine-5-carbonyl)-4,5,7,8-tetrahydropyrazolo[1,5-d][1,4]diazepin-6-yl]-3-[4-(trifluoromethoxy)phenyl]propan-1-one;

3-Cyclopropyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile;

3-Ethyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile;

3-tert-Butyl-4-[2-oxo-2-[2-(1,4,6,7-tetrahydrotriazolo[4,5-c]pyridine-5-carbonyl)-4,5,7,8-tetrahydropyrazolo[1,5-d][1,4]diazepin-6-yl]ethoxy]benzonitrile;

and pharmaceutically acceptable salts thereof.

Also particular examples of compounds of formula (I) as described herein are selected from 3-[3-fluoro-4-(trifluoromethoxy)phenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

3-(4-methoxyphenyl)-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]-3-[4-(trifluoromethoxy)phenyl]propan-1-one;

3-[3-fluoro-4-(trifluoromethoxy)phenyl]-1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]propan-1-one;

3-[3-chloro-4-(trifluoromethoxy)phenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

3-[3-chloro-4-(trifluoromethoxy)phenyl]-1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]propan-1-one;

(6-(2-cyclopropyl-6-((tetrahydro-2H-pyran-4-yl)methoxy)isonicotinoyl)-5,6,7,8-tetrahydro-4H-pyrazolo[1,5-d][1,4]diazepin-2-yl)(6,7-dihydro-1H-[1,2,3]triazolo[4,5-c]pyridin-5(4H)-yl)methanone;

(E)-3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]prop-2-en-1-one;

3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

4-methoxybenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

(3,4-difluorophenyl)methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

4-(difluoromethoxy)-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

3-fluoro-4-methoxybenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-methoxy-2-methylbenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-cyclopropylbenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[2-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[3-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

3-chloro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

2-methoxy-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

2-methyl-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-(2,2,2-trifluoroethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
[3-chloro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;
[3-chloro-4-(trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate;
3-fluoro-4-(trifluoromethoxy)benzyl 2-((3aR,7aR)-2-oxooctahydrooxazolo[5,4-c]pyridine-5-carbonyl)-8,9-dihydro-5H-[1,2,4]triazolo[1,5-d][1,4]diazepine-7(6H)-carboxylate;
and pharmaceutically acceptable salts thereof.
Further
3-Fluoro-4-(Trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
[4-(Trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;
[4-(Trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;
[4-(Trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate;
3-tert-Butyl-4-[2-oxo-2-[2-(1,4,6,7-tetrahydrotriazolo[4,5-c]pyridine-5-carbonyl)-4,5,7,8-tetrahydropyrazolo[1,5-d][1,4]diazepin-6-yl]ethoxy]benzonitrile;
and pharmaceutically acceptable salts thereof.
Also further particular examples of compounds of formula (I) as described herein are selected from
(6-(2-cyclopropyl-6-((tetrahydro-2H-pyran-4-yl)methoxy)isonicotinoyl)-5,6,7,8-tetrahydro-4H-pyrazolo[1,5-d][1,4]diazepin-2-yl)(6,7-dihydro-1H-[1,2,3]triazolo[4,5-c]pyridin-5(4H)-yl)methanone;
(E)-3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]prop-2-en-1-one;
4-(difluoromethoxy)-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
[3-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;
3-chloro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
2-methyl-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
[3-chloro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;
[3-chloro-4-(trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate;
Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

A general description of the invention is given in the following section and is outlined in FIGS. 1–4. To obtain compounds of formula (I), a suitably protected bicyclic carboxylic acid 1A is treated with an appropriate cyclic secondary amine 1B in the presence of a suitable coupling reagent such as EDC HCl, CDI, HATU or any other peptide coupling reagent in an appropriate solvent such as DMF, THF, CH$_3$CN or the like at temperatures between −20° C. and 100° C. to provide protected amide 1C. In the subsequent step, depending on the nature of the protecting group PG$_1$, various de-protection methods known to those skilled in the art can be applied to afford intermediate 1D with PG removed. For example, a BOC protecting group can be removed by treatment with organic or aqueous acids or other known methods, whereas a Z-group is often removed by hydrogenation.

Figure 1:

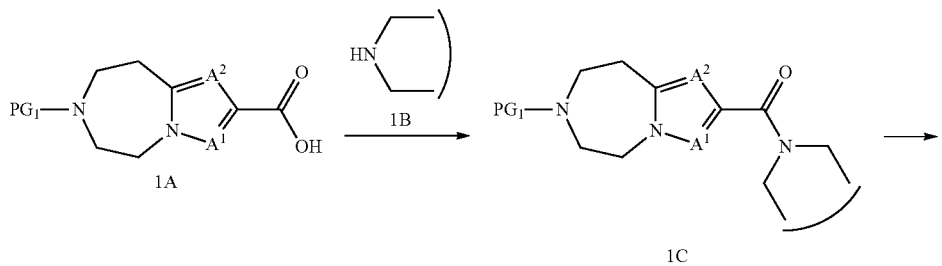

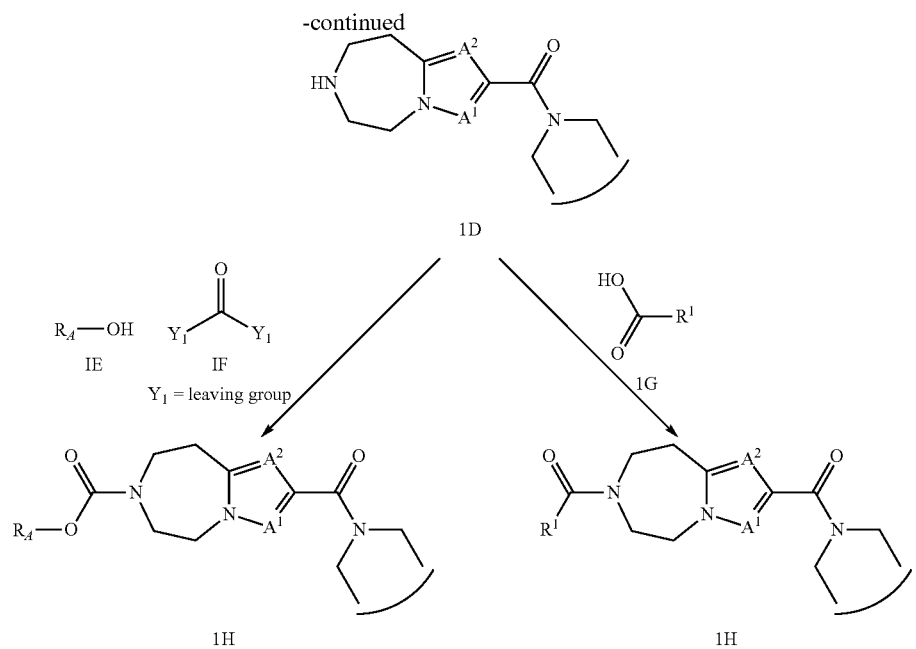

Intermediate 1D can now be treated with an alcohol 1E, wherein $R_A$ is substituted phenylalkyl, whereby 1E has been suitably activated before for example with CDI or any other type of an activated carbonic acid derivative 1F such as N,N-disuccinimidyl carbonate or phosgene or the like in the presence of a base such as triethylamine, N-methylmorpholine, Huenig's base or the like to afford the first type of examples of the current invention with the general structure 1H. The second type of examples outlined in the current invention is represented by the general structure 1I and can be made by treatment of intermediate 1D with any type of free carboxylic acid 1G (where $R_B$ is alkyl, haloalkyl, substituted cycloalkyl, substituted cycloalkylalkyl, substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl or substituted benzofuran-2-yl) in the presence of an activation agent such as CDI, EDC HCl or any type of peptide coupling reagent in the presence of a suitable base such as triethylamine, N-methylmorpholine, Huenig's base, NaOH, $Na_2CO_3$ or the like in a suitable solvent system such DMF, $CH_3CN$, THF, THF/water or similar. Alternatively, any properly activated carboxylic acid derivative such as for example an acid chloride or bromide, a mixed anhydride or a p-nitrophenolate might also be used in such a reaction.

The intermediates with fused bicycles of structure 1A or immediate precursors thereof are either described in the literature or can be made in analogy to methods described in the literature or are accessible by syntheses that can be designed by individuals skilled in the art. As an example of a synthesis of such a fused bicyclic system, the synthesis of a 6,7,8,9-tetrahydro-5H-[1,2,4]triazolo[1,5-d][1,4]diazepine-2-carboxylic acid derivative 1A with $A^1$ and $A^2$=N (equal to a structure of formula 2I) is outlined in FIG. 2. To get access to such a material, thioamide 2A where $R_C$ represents for example a small alkyl group, can be treated with a substituted hydrazine of, for example, structure 2B in a solvent such as ethanol or methanol at temperatures ranging from −20° C. to the boiling point of the solvent to provide intermediate 2C. Subsequently, intermediate 2C can be modified with a suitably protected activated β-aminocarboxylic acid derivative 2D, where $X_3$ represents a halogen or a mixed anhydride or similar, and $PG_2$ represents the protecting group, in the presence of an amine base such as triethylamine, Huenig's base, DMAP or the like in a solvent such as THF, DCM, diethylether or similar to give 2E. Hydrazine derivative 2E can be condensed to triazole 2F by heating in an appropriate solvent such as tert-BuOH, n-BuOH or similar, at temperatures ranging up to the boiling point of the solvent or by using microwave equipment. Reaction times for such a transformation can range from minutes (i.e. in a microwave at elevated temperatures and pressures) up to several days in a standard reaction flask.

Subsequent elaboration of intermediate 2F includes modification of the primary hydroxy group of 2F into a better leaving group such a tosylate or mesylate or the like by treatment with the appropriate reagent in the presence of a base such as pyridine, Huenig's base, DMAP or triethylamine or similar in an appropriate solvent such as THF, DCM or similar (if required at all) at temperatures ranging from −20° C. to the boiling point of the solvent. Removal of the protecting group $PG_2$ to afford triazole 2G depends on the nature of $PG_2$. If $PG_2$ is for example a BOC group, it can be removed by treatment with organic or aqueous acids or other known methods; if $PG_2$ is a Z-group it can usually be removed by hydrogenation. In case $PG_2$ is yet another N-protecting group, there are other suitable de-protection conditions known to those skilled in the art that need to be applied.

Starting from intermediate 2G, ring closure to give diazepine 2H can be accomplished by treatment with a base such as for example triethylamine, DMAP, $K_2CO_3$ or similar in a suitable solvent such as DMF, $CH_3CN$, THF or similar at temperatures ranging from rt up to the boiling point of the solvent. If required, a suitable N-protecting group $PG_3$ such as a BOC group, a Z-group or any other appropriate protecting group can now be re-introduced. Compatible groups as well as conditions for introduction and removal are described for example in Green & Wuts., Protective Groups in Organic Synthesis", John Wiley & Sons. Finally, if" $R_C$ is a small alkyl group, the free carboxylic acid 2I is obtained from the ester precursor 2H by hydrolysis for example in the presence of a base such as NaOH, KOH or LiOH in a solvent such as water, MeOH, EtOH, THF/water or the like at a temperature ranging from 0° C. to the boiling point of the solvent to give the desired building blocks of structure 2I. Depending on the nature of the protection group $PG_3$, other hydrolysis conditions known to those skilled in the art may also be applicable Suitably substituted benzyl alcohols 3B, wherein $R_D$ is R3, R4 and R5, as a subset of alcohols 1E, that are used for subsequent elaboration of the central cores of formula 1A are either commercially available or can be made for example from the corresponding carboxylic acids, carboxylic acid esters or aldehydes 3A ($X_4$=OH, OR or H, respectively) by reduction with suitable reducing agents such as LAH, $NaBH_4$, $LiBH_4$ or the like, optionally in the presence of additives such as $CeCl_3$, $CaCl_2$ or similar, in suitable solvents such as methanol, ethanol, THF at temperatures ranging from −20 to 100° C. (FIG. 3).

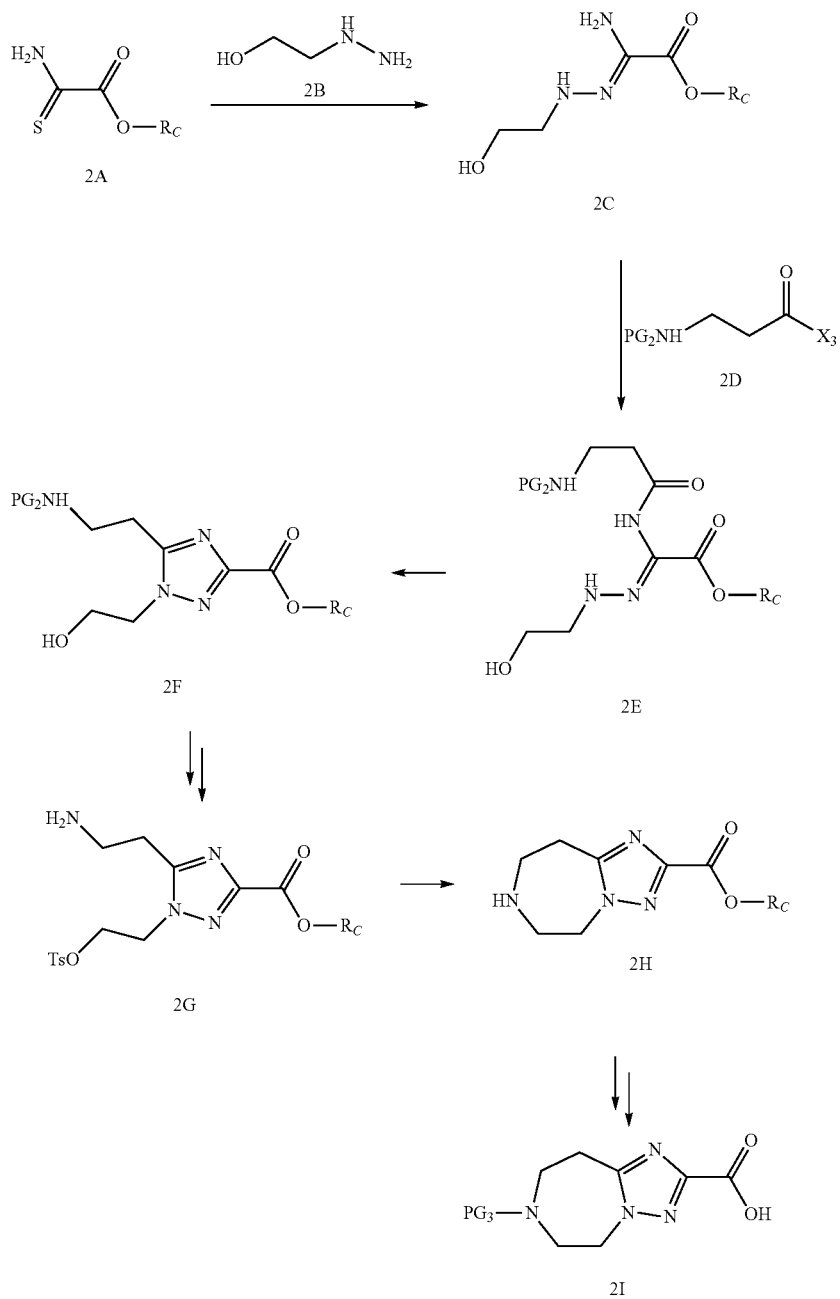

FIG. 2

FIG. 3

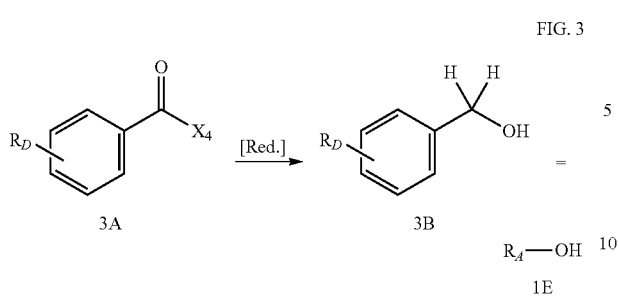

Access to suitably substituted carboxylic acids of structure 4D, wherein $R_F$ is R3, R4 and R5, as a subset of carboxylic acids 1G, can be made in several ways as shown in FIG. 4.

or can be made as outlined in FIG. 4 (lower branch). If they need to be made, they are for example accessible from the corresponding aldehydes 4E and a Wittig reagent 4F (a phosphor ylide which can have various substituents $R_E$, $R_G$, $R_H$ and $R_I$) to produce cinnamic acid derivatives 4G, using conditions well known to those skilled in the art. From cinnamic acid derivatives 4G, the corresponding 3-phenyl-propionic acid derivatives 4H are made by reduction of the double bond for example by hydrogenation in the presence of a catalyst such as for example palladium on carbon, whereby different solvents or many other catalysts can be used. Subsequently, the free carboxylic acids of structure 4D with $Y_2$=C are made under hydrolysis conditions as described above for the transformation of 4C to 4D.

FIG. 4

Phenoxyacetic acids 4D with $Y_2$=O are accessible for example from the corresponding phenols 4A (FIG. 4, upper branch) by alkylation with an appropriate acetic acid derivative 4B (for example an ester, when $R_E$ is a small alkyl group) where $X_1$ is a suitable leaving group such as a halogen or a p-toluene sulfonate or similar to give intermediate 4C. Such a transformation is usually made in the presence of a base such as potassium carbonate or cesium carbonate or the like in a suitable solvent such as DMF, acetone or CH$_3$CN at temperatures ranging from rt to the boiling point of the solvent. Similar to the conversion of 2H to 2I, ester 4C can be hydrolyzed for example in the presence of a base such as NaOH, KOH or LiOH or the like to give the desired building blocks of structure 4D with $Y_2$=O.

Appropriately substituted 3-phenylpropionic acids of structure 4D with $Y_2$=C are either commercially available Other carboxylic acids that are needed as intermediates to prepare some of the Autotaxin inhibitors shown as examples in this application are made differently. FIG. 5 shows the general route for the synthesis of appropriately substituted oxo-pyridine-4-carboxylic acids 5A:

FIG. 5

-continued

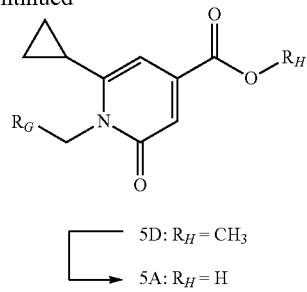

5D: $R_H = CH_3$
5A: $R_H = H$

Methyl 6-cyclopropyl-2-oxo-1H-pyridine-4-carboxylate (5B), for example, which is commercially available or can be made from the corresponding carboxylic acid by esterification under conditions known to those skilled in the art, can be alkylated with an appropriate alkyl halide 5C, where X is a chloro, bromo or iodo atom, in the presence of a suitable base such as sodium hydride, lithium diisopropylamide, potassium carbonate or cesium carbonate or the like in an appropriate solvent such as DMF, THF or similar to provide the substituted pyridone intermediate 5D. This material is easily converted to the free carboxylic acid 5A under hydrolytic conditions as described above, e. g. for the conversion of 4C to 4D.

Also an embodiment of the present invention is a process to prepare a compound of formula (I) as defined above comprising the reaction of a compound of formula (II) in the presence of a compound of formula (III);

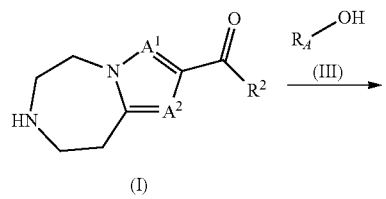
(I)

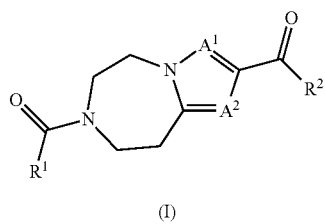
(I)

wherein $R^1$ is phenylalkoxy substituted with $R^3$, $R^4$ and $R^5$, $R_A$ is phenylalkyl substituted with $R^3$, $R^4$ and $R^5$ and $R^2$, $R^3$, $R^4$, $R^5$, $A^1$ and $A^2$ are as defined above.

In particular, in the presence of an activating agent such as CDI, N,N-disuccinimidyl carbonate or phosgene, preferably N,N-disuccinimidyl, in a solvent such as acetronitrile, in the presence of a base such as triethylamine, N-methylmorpholine or Huenig's base and at a temperature comprised between −10° C. and room temperature.

Another embodiment of the present invention is a process to prepare a compound of formula (I) as defined above comprising the reaction of a compound of formula (II) in the presence of a compound of formula (IV);

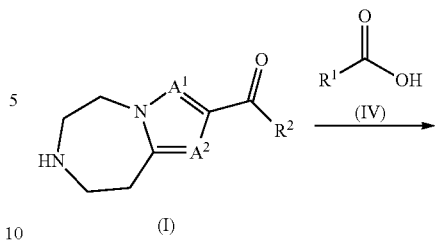
(I)

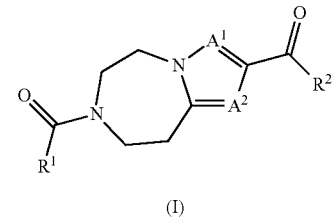
(I)

wherein $R^1$ is alkyl, haloalkyl, substituted cycloalkyl, substituted cycloalkylalkyl, substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl or substituted benzofuran-2-yl, wherein substituted cycloalkyl, substituted cycloalkylalkyl, substituted phenyl, substituted phenyl alkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl and substituted benzofuran-2-yl are substituted with $R^3$, $R^4$ and $R^5$ and $R^2$, $R^3$, $R^4$, $R^5$, $A^1$ and $A^2$ are as defined above.

In particular, in the presence of an activation agent such as CDI, EDC HCl, in a solvent such as DMF, $CH_3CN$, THF, THF/water, in the presence of a base such as triethylamine, N-methylmorpholine, Huenig's base, NaOH, $Na_2CO_3$.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

In a particular embodiment, the compounds of formula (I) or their pharmaceutically acceptable salts and esters can be used for the treatment or prophylaxis of organ or skin fibrosis.

In another embodiment, the fibrotic disease is renal tubulo-interstitial fibrosis or glomerulosclerosis.

In another embodiment, the fibrotic disease is non-alcoholic liver steatosis, liver fibrosis or liver cirrhosis.

In another embodiment, the fibrotic disease is idiopathic pulmonary fibrosis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like.

Metabolic conditions include, but are not limited to, obesity and diabetes.

In another embodiment, the compounds of formula (I) or their pharmaceutically acceptable salts and esters can be used for the treatment or prophylaxis of cholestatic or non-cholestatic chronic pruritus.

The present invention also relates to the use of a compound according to formula (I) as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the treatment or prophylaxis of renal conditions, liver conditions and fibrotic diseases.

A particular embodiment of the present invention is a compound according to formula (I) as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula (I) as described herein for the treatment or prophylaxis of renal conditions, liver conditions and fibrotic diseases.

The present invention also relates to the use of a compound according to formula (I) as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula (I) as described herein.

Also an object of the invention is a method for the treatment or prophylaxis of renal conditions, liver conditions and fibrotic diseases, which method comprises administering an effective amount of a compound according to formula (I) as described herein.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the inflammatory condition is arthritis.

In a particular embodiment, the condition of the nervous system is neuropathic pain.

In another embodiment, the fibrotic disease is encapsulating peritonitis

In another embodiment, the fibrotic disease is idiopathic pulmonary fibrosis.

In another embodiment, the fibrotic disease is non-alcoholic liver steatosis, liver fibrosis or liver cirrhosis.

Also an embodiment of the present invention are compounds of formula (I) as described herein, when manufactured according to any one of the described processes.

Assay Procedures

Production of Human Full Length Autotaxin (ATX) with and without His Tag

Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultra-filtration by adding Brij 35 to a final concentration of 0.02% and by adjusting the pH to 7.0 using 1 M HCl. Then the supernatant was first microfiltred through a 0.2 µm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 µM MR121 substrate in DMSO), diluted to 2-5× final concentration in assay buffer.

Test compounds (10 mM stock in DMSO, 8 µL) were obtained in 384 well sample plates (Corning Costar #3655) and diluted with 8 µL DMSO. Row-wise serial dilutions were made by transferring 8 µL cpd solution to the next row up to row 0. The compound and control solutions were mixed five times and 2 µL were transferred to 384 well assay plates (Corning Costar #3702). Then, 15 µL of 41.7 nM ATX solution was added (30 nM final concentration), mixed five times and then incubated for 15 minutes at 30° C. 10 µL of MR121 substrate solution was added (1 µM final concentration), mixed 30 times and then incubated for 15 minutes at 30° C. Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

Inhibitory activities ($IC_{50}$) for the examples of the present invention against ATX are given below.

| Example | IC50 (µM) |
|---|---|
| 1 | 0.158 |
| 2 | 2.01 |
| 3 | 0.018 |
| 4 | 0.007 |
| 5 | 0.002 |
| 6 | 0.004 |
| 7 | 0.07 |
| 8 | 0.06 |
| 9 | 0.006 |
| 10 | 0.018 |
| 11 | 0.015 |
| 12 | 0.067 |
| 13 | 0.017 |
| 14 | 0.014 |
| 15 | 0.011 |
| 16 | 0.012 |
| 17 | 0.010 |
| 18 | 0.013 |
| 19 | 0.151 |
| 20 | 0.006 |
| 21 | 0.017 |
| 22 | 0.018 |
| 23 | 0.050 |
| 24 | 0.009 |
| 25 | 0.007 |
| 26 | 0.016 |
| 27 | 0.052 |
| 28 | 0.076 |
| 29 | 0.038 |
| 30 | 0.041 |
| 31 | 0.022 |
| 32 | 0.030 |
| 33 | 0.094 |
| 34 | 0.007 |
| 35 | 0.013 |
| 36 | 0.006 |
| 37 | 0.009 |
| 38 | 0.021 |
| 39 | 0.014 |
| 40 | 0.017 |
| 41 | 0.006 |
| 42 | 0.007 |
| 43 | 0.056 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

Intermediates

Abbreviations aq.=aqueous; CAS=Chemical Abstracts Service Registry Number; e.r.=enantiomeric ratio; HPLC=high performance liquid chromatography; MS=mass spectrum; NMR=nuclear magnetic resonance spectrum; sat.=saturated; rt=room temperature. Other abbreviations such as abbreviations for chemical reagents or solvents are known to those skilled in the art.

Intermediate 1

6-Phenylmethoxycarbonyl-4,5,7,8-tetrahydropyrazolo[1,5-d][1,4]diazepine-2-carboxylic acid

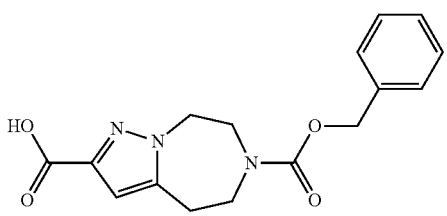 [SMILES: O=C(O)c1cc2n(n1)CCN(C(=O)OCc1ccccc1)CC2]

(6-O-benzyl 2-O-ethyl 4,5,7,8-tetrahydropyrazolo[1,5-d][1,4]diazepine-2,6-dicarboxylate, CAS: 1080027-19-5; synthesized in steps 1-7 described below) has been mentioned in Gerlach et al., PCT Int. Appl. (2008), WO 2008135526 A1 and was synthesized in analogy to Venkatesan M. A. et al., J. Med. Chem. 2006, 49, 4623.

Step 1: tert-Butyl 1,4-dibenzyl-1,4-diazepane-5-carboxylate

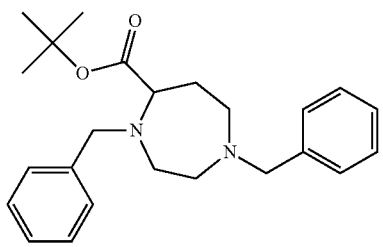 [SMILES: CC(C)(C)OC(=O)C1CCN(Cc2ccccc2)CCN1Cc1ccccc1]

In a 20 mL round-bottomed flask, tert-butyl-2,4-dibromobutanoate (500 mg, [CAS: 77629-96-0]), N,N'-dibenzylethylenediamine (372 mg, [CAS: 140-28-3]) and triethylamine (460 mg) were dissolved in dichloromethane (20 mL) to give a colorless solution. The mixture was heated to 40° C. for 15 hours. The reaction mixture was poured into ice/water and basified with saturated NaHCO$_3$ solution. The aqueous phase was then extracted two times with dichloromethane. The combined organic layers were dried over Na$_2$SO$_4$, filtered and the solvent was evaporated to dryness. The crude material was purified by flash chromatography (silica gel, gradient of ethyl acetate in heptane) to give the title compound as a light brown oil (232 mg, 35%). MS (EI): 380.0 [M$^+$].

Step 2: tert-Butyl 1,4-diazepane-5-carboxylate

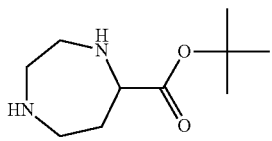

tert-Butyl 1,4-dibenzyl-1,4-diazepane-5-carboxylate (3.40 g) was dissolved in ethanol (50 mL) to give a light brown solution. Palladium on activated charcoal (800 mg, 10% Pd) was added and an atmosphere of hydrogen was introduced at room temperature. The mixture was stirred under hydrogen for 9 hours at 5 bars. The reaction mixture was filtered over dicalite speed plus (Acros Organics) and the solvent was evaporated to dryness to give the title compound as a light brown oil (1.40 g, 77%). MS (m/e): 201.7 [M+H]$^+$.

Step 3: 1-O-benzyl 5-O-tert-butyl 1,4-diazepane-1,5-dicarboxylate

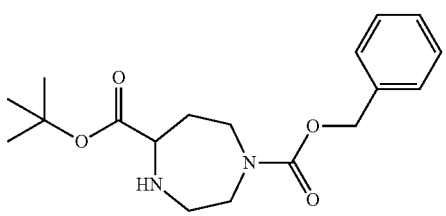 [SMILES: CC(C)(C)OC(=O)C1CCN(C(=O)OCc2ccccc2)CCN1]

tert-Butyl 1,4-diazepane-5-carboxylate (1.055 g) was dissolved in dichloromethane (20 mL) to give a light brown solution at room temperature under an argon atmosphere. The mixture was cooled down to 0° C. and a solution of dibenzyl dicarbonate (1.51 g) in dichloromethane (10 mL) was added drop wise over a period of 10 minutes. The reaction mixture was stirred for 30 minutes at 0° C. and then warmed up to rt for 1.5 hours. The mixture was directly evaporated to dryness and the residue was purified by flash chromatography (silica gel, gradient of methanol in dichloromethane) to give the title compound as a light brown oil (960 mg, 52%). MS (m/e): 335.6 [M+H]$^+$.

Step 4: 1-Phenylmethoxycarbonyl-1,4-diazepane-5-carboxylic acid 2,2,2-trifluoroacetate

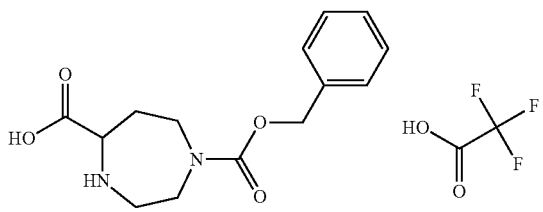 [SMILES: O=C(O)C1CCN(C(=O)OCc2ccccc2)CCN1 ; O=C(O)C(F)(F)F]

1-O-benzyl 5-O-tert-butyl 1,4-diazepane-1,5-dicarboxylate (9.0 g) was dissolved in dichloromethane (90 mL) at room temperature under an argon atmosphere. Then, 2,2,2-trifluoroacetic acid (30.7 g, 20.70 mL) was added drop wise over a period of 15 minutes. The mixture was stirred at room temperature for 8 hours. The solvent was directly evaporated and the residue was dried at high vacuum to give the title compound as a crude light brown oil (11 g, 100%, purity 95%). MS (m/e): 279.6 [M-TFA+H]$^+$.

Step 5: 4-Nitroso-1-phenylmethoxycarbonyl-1,4-diazepane-5-carboxylic acid

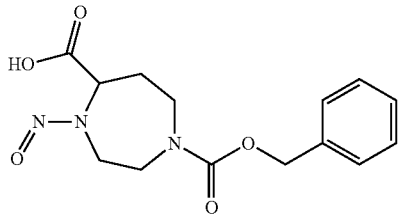 [SMILES: O=NN1CCN(C(=O)OCc2ccccc2)CCC1C(=O)O]

1-(Benzyloxycarbonyl)-1,4-diazepane-5-carboxylic acid 2,2,2-trifluoroacetic acid (1.448 g) was dissolved in water (11.0 mL) and tetrahydrofuran (4.0 mL) at room temperature. Then, hydrochloric acid (37%, 337 µL) was added dropwise over a period of 5 minutes. The light brown solution was cooled down to 0° C. and sodium nitrite (251 mg) was added. The mixture was warmed up to room temperature and stirring was continued for 1 hour. The reaction mixture was poured into ice/water. The aqueous phase was then extracted two times with ethyl acetate.

The combined organic layers were washed with brine, dried over $Na_2SO_4$, filtered and evaporated. The residue was dried at high vacuum to give the title compound as a crude light brown oil (966 mg, 97%, purity 80%). MS (m/e): 308.5 $[M+H]^+$.

Step 6: 6-Phenylmethoxycarbonyl-4,5,7,8-tetrahydrooxadiazolo[3,4-d][1,4]diazepin-9-ium-3-olate

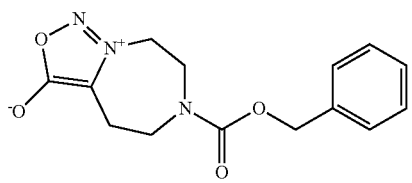

1-(Benzyloxycarbonyl)-4-nitroso-1,4-diazepane-5-carboxylic acid (936 mg) was dissolved in acetonitrile (15 mL) at room temperature under an argon atmosphere. The mixture was cooled down to 0° C. and trifluoroacetic anhydride (768 mg) was added drop wise over a period of 10 minutes. The mixture was warmed up to room temperature and stirring was continued for 3 hours. Then, potassium carbonate (505 mg) was added and the mixture was stirred for 30 minutes. The reaction mixture was poured into ice/water. The aqueous phase was then extracted two times with ethyl acetate. The combined organic layers were washed with brine, dried over $Na_2SO_4$, filtered and evaporated. The crude material was purified by flash chromatography (silica gel, gradient of ethyl acetate in heptane) to give the title compound as a light yellow gum (300 mg, 39%). MS (m/e): 290.5 $[M+H]^+$.

Step 7: 6-O-benzyl 2-O-ethyl 4,5,7,8-tetrahydropyrazolo[1,5-d][1,4]diazepine-2,6-dicarboxylate

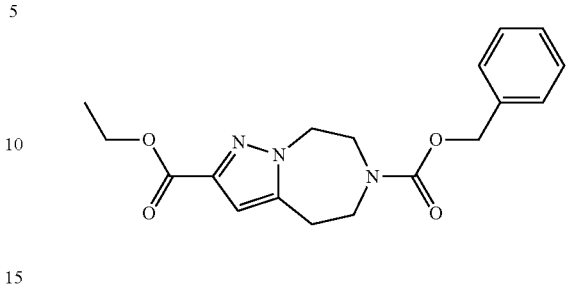

Ethyl propiolate (284 mg) was added to a solution of 6-(benzyloxycarbonyl)-5,6,7,8-tetrahydro-4H-[1,2,3]oxadiazolo[3,4-d][1,4]diazepin-9-ium-3-olate (186 mg) in chlorobenzene (4.0 mL) at room temperature under an argon atmosphere. The mixture was heated at 150° C. for 2 hours in a microwave. The reaction mixture was directly evaporated to dryness. The crude material was purified by flash chromatography (silica gel, gradient of ethyl acetate in heptane) to give the title compound as a light yellow gum (131 mg, 53%). MS (m/e): 344.5 $[M+H]^+$.

The regioisomer 6-O-benzyl 3-O-ethyl 4,5,7,8-tetrahydropyrazolo[1,5-d][1,4]diazepine-3,6-dicarboxylate was also isolated by flash chromatography (silica gel, gradient of ethyl acetate in heptane) as a light yellow gum (36 mg, 16%). MS (m/e): 344.5 $[M+H]^+$.

Step 8: 6-Phenylmethoxycarbonyl-4,5,7,8-tetrahydropyrazolo[1,5-d][1,4]diazepine-2-carboxylic acid

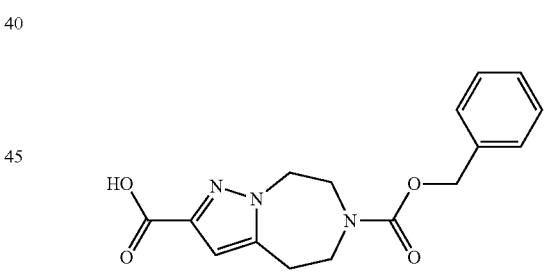

Lithium hydroxide 1M solution (9.33 mL) was added drop wise over a period of 10 minutes to a solution of 6-benzyl 2-ethyl 7,8-dihydro-4H-pyrazolo[1,5-d][1,4]diazepine-2,6(5H)-dicarboxylate (1.78 g) in tetrahydrofuran (20 mL) at room temperature. The mixture was stirred at room temperature for 18 hours. The reaction mixture was poured into ice/water and acidified with HCl (2M) solution to pH=1. The aqueous phase was then extracted two times with ethyl acetate. The combined organic layers were washed with brine, dried over $Na_2SO_4$, filtered and the solvent was evaporated. The residue was dried at high vacuum to give the title compound as a yellow solid (1.64 g, 95%). MS (m/e): 316.5 $[M+H]^+$.

Intermediate 2

4,5,7,8-tetrahydro-1,3,3a,6-tetraaza-azulene-2,6-dicarboxylic acid 6-tert-butyl ester

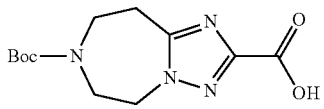

Step 1: Ethyl (2Z)-2-amino-2-(2-hydroxyethylhydrazono)acetate

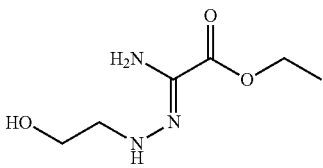

To a solution of amino-thioxo-acetic acid ethyl ester (5.0 g) in ethanol (160 mL) at 0° C. was added 2-hydrazino-ethanol and the reaction mixture was stirred at 25° C. for 2 h. Volatile components were then removed in vacuo to get the title compound (6.58 g) as yellow sticky solid that was used in next step without any further purification. LC-MS: 175.8 [M+H]⁺.

Step 2: Ethyl (2Z)-2-[3-(tert-butoxycarbonylamino)propanoylamino]-2-(2-hydroxyethylhydrazono)acetate

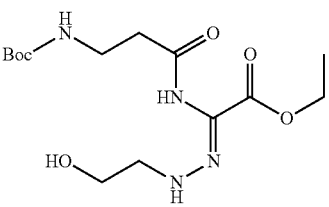 [SMILES: CCOC(=O)/C(=N/NCCO)NC(=O)CCNC(=O)OC(C)(C)C]

To a solution of 3-tert-butoxycarbonylamino-propionic acid (7.73 g) in THF (100 mL) at −10° C. were added triethyl amine (6.78 mL) and ethyl chloroformate (4.64 mL) under a nitrogen atmosphere and the reaction mixture was stirred at −10° C. for 0.5 h. The reaction mixture was filtered and the filtrate was then added to a solution of ethyl (2Z)-2-amino-2-(2-hydroxyethylhydrazono)acetate (6.57 g) and the mixture was stirred at 25° C. for 16 h. Solvent was evaporated in vacuo and the residue was partitioned between ethyl acetate (150 mL) and water (100 mL). The organic layer was separated, and aqueous layer was re-extracted with ethyl acetate (2×100 ml). The combined organic layers were washed with brine, dried over anhydrous $Na_2SO_4$, filtered, and concentrated in vacuo. The crude material was purified by column chromatography over normal silica gel (20-40% EtOAc/hexane) to get (3-tert-butoxycarbonylamino-propionylamino)-[(2-hydroxy-ethyl)-hydrazono]-acetic acid ethyl ester (5.81 g) as yellow sticky solid. LC-MS: 346.9 [M+H]⁺.

Step 3: Ethyl 5-[2-(tert-butoxycarbonylamino)ethyl]-1-(2-hydroxyethyl)-1,2,4-triazole-3-carboxylate

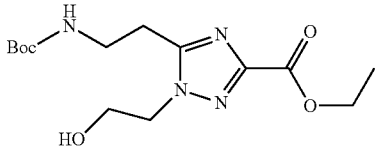 [SMILES: CCOC(=O)c1nc(CCNC(=O)OC(C)(C)C)n(CCO)n1]

As solution of ethyl (2Z)-2-[3-(tert-butoxycarbonylamino)propanoylamino]-2-(2-hydroxyethylhydrazono)acetate (5.8 g) in n-BuOH (400 mL) was refluxed for 18 h. The solvent was removed in vacuo and the residue was purified by column chromatography over normal silica gel using (0-4% MeOH/DCM as an eluent) to afford a mixture of 5-(2-tert-butoxycarbonyl-amino-ethyl)-1-(2-hydroxy-ethyl)-1H-[1,2,4]triazole-3-carboxylic acid ethyl ester and corresponding n-butyl ester (4.22 g, impure) as yellow sticky solid. LC-MS: 329.2 and 356.9 [M+H]⁺.

Step 4: Ethyl 5-(2-tert-butoxycarbonylamino-ethyl)-1-[2-(toluene-4-sulfonyloxy)-ethyl]-1H-[1,2,4]triazole-3-carboxylate

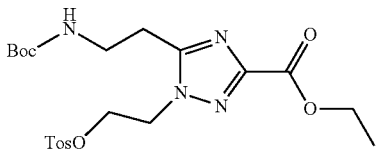

To a solution of 5-(2-tert-butoxycarbonyl amino-ethyl)-1-(2-hydroxy-ethyl)-1H-[1,2,4]triazole-3-carboxylic acid ethyl ester (4.2 g) in DCM (100 mL) at 0° C. were added triethyl amine (2.70 mL) and p-toluenesulfonyl chloride (2.92 g) and reaction mixture was stirred at 25° C. for 16 h. The reaction mixture was diluted with DCM (50 mL) and washed with saturated aqueous sodium bicarbonate solution (100 mL). The organic layer was dried over anhydrous $Na_2SO_4$, filtered, and concentrated in vacuo. The residue was purified by column chromatography over normal silica gel (10-30% EtOAc/hexane as an eluent) to afford the title compound as a mixture of the ethyl ester and the corresponding butyl ester (1.98 g) as yellow sticky solid. LC-MS: 482.9 and 511.1 [M+H]⁺.

Step 5: Ethyl 5-(2-amino-ethyl)-1-(2-hydroxy-ethyl)-1H-[1,2,4]triazole-3-carboxylate

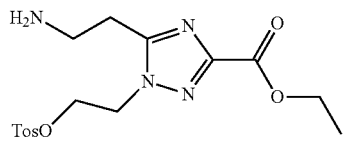

To a solution of ethyl 5-(2-tert-butoxycarbonylamino-ethyl)-1-[2-(toluene-4-sulfonyloxy)-ethyl]-1H-[1,2,4]triazole-3-carboxylate (5.17 g) in DCM (100 mL) was added 4N HCl in dioxane (40 mL) and the reaction mixture was stirred at 25° C. for 2 h. Then the volatile components were removed in vacuo to afford the title compound as a mixture of the ethyl ester and the corresponding butyl ester hydrochloride salts (4.42 g, crude) as brown sticky solid. LC-MS: 383.1 and 410.8 [M+H]$^+$.

Step 6: Ethyl 5,6,7,8-tetrahydro-4H-1,3,3a,6-tetraaza-azulene-2-carboxylate

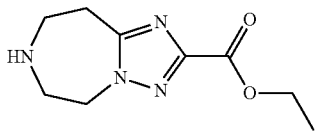

To a suspension of ethyl 5-(2-amino-ethyl)-1-(2-hydroxy-ethyl)-1H-[1,2,4]triazole-3-carboxylate (4.4 g, crude) in THF (200 mL) was added drop wise triethylamine (4.44 mL) at 0° C. and the reaction mixture was stirred at 60° C. for 18 h. Volatilities were removed in vacuo to get the title compound as a mixture of the ethyl ester and the corresponding butyl ester along with other impurities (2.23 g, crude) as brown sticky solid that was used in next step with out further purification. LC-MS: 211.3 and 239.0 [M+H]$^+$.

Step 7: 4,5,7,8-Tetrahydro-1,3,3a,6-tetraaza-azulene-2,6-dicarboxylic acid 6-tert-butyl ester 2-ethyl ester

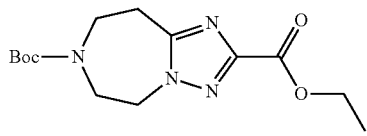 [SMILES: CCOC(=O)c1nc2n(n1)CCN(C(=O)OC(C)(C)C)CC2]

To a suspension of ethyl 5, 6, 7, 8-tetrahydro-4H-1, 3, 3a, 6-tetraaza-azulene-2-carboxylate (2.2 g) in THF (100 mL) were added triethyl amine (2.21 mL) and di-tert-butyl carbonate (3.6 mL), and the reaction mixture was stirred at 25° C. for 2 h. The solvent was removed in vacuo, and the residue was purified by column chromatography over normal silica gel (0-5% MaOH/DCM as an eluent) to afford the title compound as a mixture of the ethyl ester and the corresponding butyl ester (1.2 g, 53.3% from ethyl 5-(2-tert-butoxycarbonyl amino-ethyl)-1-[2-(toluene-4-sulfonyloxy)-ethyl]-1H-[1,2,4]triazole-3-carboxylate, obtained in Step 4) as yellow sticky solid. LC-MS: 311.2 and 339.1 [M+H]$^+$.

Step 8: 4,5,7,8-Tetrahydro-1,3,3a,6-tetraaza-azulene-2,6-dicarboxylic acid 6-tert-butyl ester

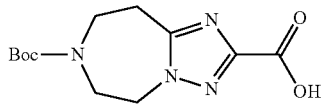

To a solution of 4,5,7,8-tetrahydro-1,3,3a,6-tetraaza-azulene-2,6-dicarboxylic acid 6-tert-butyl ester 2-ethyl ester (1.2 g) in THF (16 mL) at 25° C. was added a solution of LiOH H$_2$O (324 mg) in water (4 mL), and the reaction mixture was stirred at 25° C. for 1 h. The solvent was removed in vacuo and the residue was dissolved in water (30 mL) and washed with ethyl acetate. The aqueous layer was acidified with saturated aqueous citric acid solution and extracted with DCM (3×75 mL). The combined organic layers were dried over anhydrous Na$_2$SO$_4$, filtered, and concentrated in vacuo. The residue was purified by prep. HPLC to afford the title compound (228 mg, 21%) as off white solid. LC-MS: 283.3 [M+H]$^+$.

Intermediate 3

5,6,8,9-tetrahydro-imidazo[1,2-a][1,4]diazepine-2,7-dicarboxylic acid 7-benzyl ester

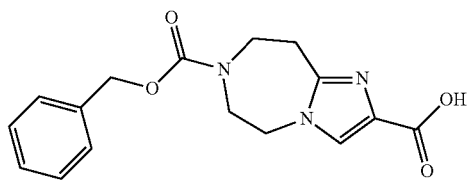 [SMILES: O=C(O)c1cn2c(n1)CCN(C(=O)OCc1ccccc1)CC2]

2-Formyl-5,6,8,9-tetrahydro-imidazo[1,2-a][1,4]diazepine-7-carboxylic acid benzyl ester (500 mg), made according to the procedures described by Gerlach et al. in PCT Int. Appl. (2008), WO 2008135526 A1, was dissolved in acetone (15 mL) and water (15 mL). Then, sulphamic acid (292 mg) and NaClO$_2$ (211 mg) were added, and the reaction mixture was stirred at 25° C. for 3 h. Acetone was removed in vacuo, and the aqueous layer was extracted with DCM (3×50 mL). The combined organic layers were dried over anhydrous Na$_2$SO$_4$, filtered, and concentrated in vacuo. The crude material was triturated with Et$_2$O and to provide an off-white solid that was dried to yield 5,6,8,9-tetrahydro-imidazo[1,2-a][1,4]diazepine-2,7-dicarboxylic acid 7-benzyl ester (6) (425 mg, 81%). LC-MS: 316.0 [M+H]$^+$.

Intermediate 4

4-(hydroxymethyl)-3-isopropyl-benzonitrile

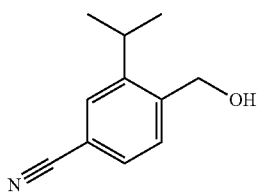

Step 1: 4-cyano-2-isopropylphenyl trifluoromethanesulfonate

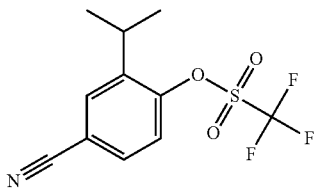 [SMILES: CC(C)c1cc(C#N)ccc1OS(=O)(=O)C(F)(F)F]

To a solution of pyridine (915 µl) in dichloromethane (70 mL) was added trifluoromethanesulfonic anhydride (1.75 mL) at 0° C. The white suspension was stirred for 10 min. at 0° C. A solution of 4-hydroxy-3-isopropylbenzonitrile (CAS: 1.52 g) in dichloromethane (40 ml) was added dropwise. The ice-bath was removed and the dark brown clear solution was stirred at rt. TLC at t=75 min showed the reaction to be complete. The reaction mixture was diluted with dichloromethane and washed with water and brine. The aq. layers were back extracted with dichloromethane dried over magnesium sulfate filtered and evaporated. The residue was purified by flash chromatography (100 g, SiO₂; gradient heptane/dichloromethane 9:1 to heptane/dichloromethane 4:6) to afford the title compound (2.63 g, 95%). Yellow liquid; MS: 292.1 [M−H]⁻.

Step 2: Methyl 4-cyano-2-isopropylbenzoate

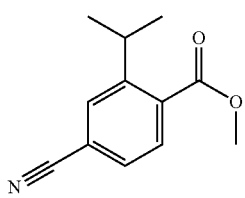

4-Cyano-2-isopropylphenyl trifluoromethanesulfonate (2.30 g) was added to an autoclave and methanol (46 mL) was added. The autoclave was set under argon and then triethylamine (2.73 mL) and 1,1'-bis(diphenylphosphino)ferrocene-palladium(II)dichloride dichloromethane complex (320 mg) were added. A CO atmosphere was introduced by repeated (3 times) evacuation and introduction of 10 bar CO. The pressure was then increased to 50 bar and the autoclave was kept at 110° C. for 20 hrs. The reaction mixture was cooled to rt and the red solution was evaporated in vacuo. Filtration of the residue over 100 g SiO₂ column, solvent dichloromethane/heptane 1:1 afforded the title compound (1.23 g, 77%). Light yellow oil, MS: 218.5 [M+H]⁺.

Step 3: 4-(hydroxymethyl)-3-isopropyl-benzonitrile

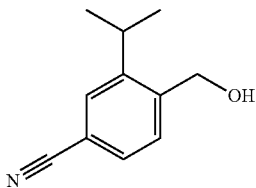

To a clear, light yellow solution of methyl 4-cyano-2-isopropylbenzoate (1.227 g) in tetrahydrofuran (15 mL) was added lithium borohydride (2M in THF, 9.06 mL). The reaction mixture was heated to reflux. TLC (dichloromethane/heptane 4:1) at t=1 h showed the reaction was complete. The reaction was cooled to room temperature and 5 mL MeOH was added. After 30 min, the reaction was diluted with ethyl acetate and extracted with water and brine. The aq. layers were back-extracted with ethyl acetate. The combined organic layers were dried over magnesium sulfate filtered and evaporated. Chromatography (100 g, SiO₂; gradient dichloromethane to dichloromethane/methanol+ 0.25% aq. NH₄OH solution 19:1) afforded the title compound (802 mg, 76%). Light yellow oil, MS: 176.2 [M+H]⁺.

Intermediate 5

N-[5-cyano-2-(hydroxymethyl)phenyl]-2,2-dimethyl-propanamide

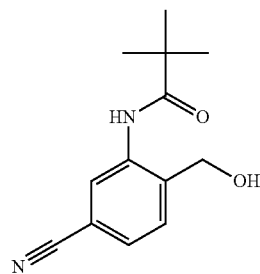

Step 1: Methyl 4-cyano-2-pivalamidobenzoate

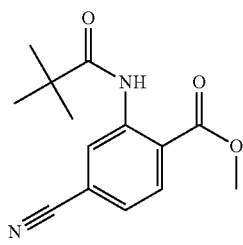 [SMILES: COC(=O)c1ccc(C#N)cc1NC(=O)C(C)(C)C]

To a clear, red solution of methyl 2-amino-4-cyanobenzoate (CAS: 159847-83-3; 776 mg) in pyridine (6 mL) was added pivaloyl chloride (650 µl) dropwise at 0° C. A solid precipitated. MS at t=2 h showed the reaction to be complete. The reaction mixture was diluted with 1M aq. HCl and extracted 2 times with ethyl acetate/2-methyltetrahydrofurane. The combined organic layers were washed with water, 50% Na₂CO₃ solution and brine dried over magnesium sulfate filtered and evaporated. The residue was suspended in ethyl acetate to afford the title compound (819 mg, white solid). The mother liquid was evaporated and the residue treated with tBME to afford another crop of the title compound (148 mg, white solid). The products were combined to afford the title compound (967 mg, 84%). White solid. MS: 261.1 [M−H]⁻.

Step 2: N-[5-cyano-2-(hydroxymethyl)phenyl]-2,2-dimethyl-propanamide

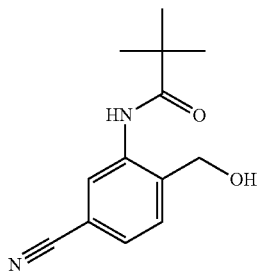 [SMILES: CC(C)(C)C(=O)Nc1cc(C#N)ccc1CO]

To a white suspension of methyl 4-cyano-2-pivalamido-benzoate (335 mg) in tetrahydrofuran (6.0 mL) was added a solution of calcium chloride (286 mg) in ethanol (6.0 mL) under argon. Sodium borohydride (195 mg) was added in 3 portions over a period of 20 minutes. TLC at t=4 h showed the reaction to be complete. The reaction mixture was poured onto ice/water and sat. NH₄Cl solution. The aq. layer was extracted two times with ethyl acetate. The combined organic layers were washed with brine, dried over magnesium sulfate, filtered and evaporated. Chromatography (50 g, SiO2, gradient dichloromethane to dichloromethane/methanol 9:1) afforded the title compound (257 mg, 86%). White solid, MS: 233.2 [M+H]⁺.

Intermediate 6

2-(4-cyano-2-cyclopropylphenoxy)acetic acid

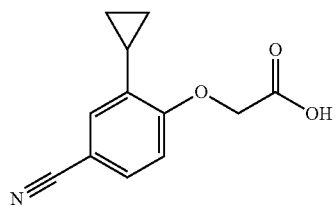 [SMILES: N#Cc1ccc(OCC(=O)O)c(C2CC2)c1]

Step 1: Ethyl 2-(4-cyano-2-cyclopropylphenoxy)acetate

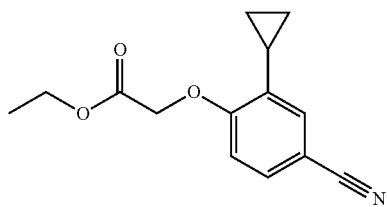 [SMILES: CCOC(=O)COc1ccc(C#N)cc1C1CC1]

3-Cyclopropyl-4-hydroxybenzonitrile (140 mg) was dissolved in acetone (5 mL) at rt under an argon atmosphere. Potassium carbonate (122 mg) and ethyl 2-bromoacetate (97 µL) were successively added to the mixture. The reaction mixture was heated to reflux for 3 hours and then cooled down to rt. The solvent was evaporated and the residue was poured into brine and ethyl acetate and the layers were separated. The aqueous layer was extracted twice with additional ethyl acetate. The organic layers were combined washed once with brine, dried over Na₂SO₄, filtered, evaporated and dried at high vacuum to give the crude product as a yellow viscous oil that was used without further purification (210 mg, 88%).

Step 2: 2-(4-cyano-2-cyclopropylphenoxy)acetic acid

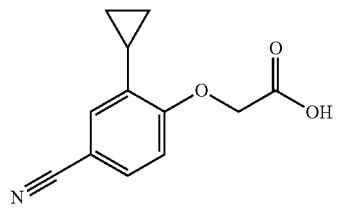

Lithium hydroxide 1M solution (1.47 mL) was added drop wise over a period of 5 minutes to a solution of ethyl 2-(4-cyano-2-cyclopropylphenoxy)acetate (200 mg) in THF (4.0 ml) at room temperature. The mixture was stirred at room temperature for 5 hours. The reaction mixture was poured into ice/water and acidified with HCl 2M solution to pH=1. The aqueous phase was then extracted two times with ethyl acetate. The combined organic layers were washed with brine, dried over Na₂SO₄, filtered and the solvent was evaporated. The residue was dried at high vacuum to give the title compound as a yellow solid (170 mg, 96%). MS (m/e): 216.1 [M−H]⁻.

Intermediate 7

2-(4-cyano-2-ethylphenoxy)acetic acid

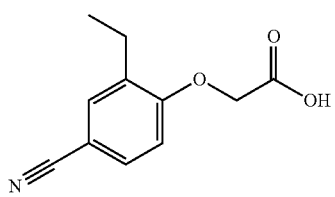

This material was made in analogy to Intermediate 6 from 3-ethyl-4-hydroxybenzonitrile (CAS: 4997-55-1)

Intermediate 8

2-(2-tert-butyl-4-cyanophenoxy)acetic acid

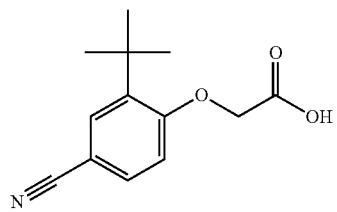 [SMILES: CC(C)(C)c1cc(C#N)ccc1OCC(=O)O]

This material was made in analogy to Intermediate 7 from 3-tert-butyl-4-hydroxybenzonitrile (CAS: 4910-04-7)

Intermediate 9

5,6,7,8-Tetrahydro-4H-pyrazolo[1,5-d][1,4]diazepin-2-yl(1,4,6,7-tetrahydrotriazolo[4,5-c]pyridin-5-yl)methanone

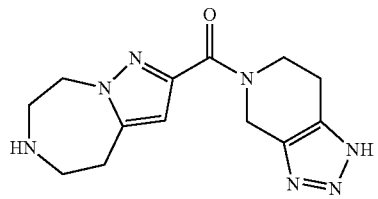 [SMILES: O=C(c1cc2n(n1)CCNCC2)N1CCc2[nH]nnc2C1]

The synthesis of Intermediate 9 is described in Example 3, Step 1.

Intermediate 10

1,4,6,7-tetrahydrotriazolo[4,5-c]pyridin-5-yl(6,7,8,9-tetrahydro-5H-[1,2,4]triazolo[1,5-d][1,4]diazepin-2-yl)methanone hydrochloride

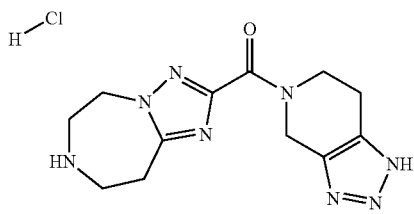 [SMILES: Cl ; O=C(c1nc2n(n1)CCNCC2)N1CCc2[nH]nnc2C1]

Step 1: Tert-butyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate

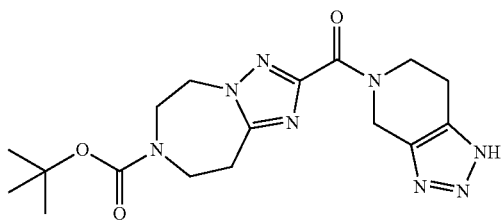 [SMILES: CC(C)(C)OC(=O)N1CCc2nc(C(=O)N3CCc4[nH]nnc4C3)nn2CC1]

In a 20 mL round-bottom flask, 7-(tert-butoxycarbonyl)-6,7,8,9-tetrahydro-5H-[1,2,4]triazolo[1,5-d][1,4]diazepine-2-carboxylic acid (Intermediate 9, 450 mg) and 4,5,6,7-tetrahydro-1H-[1,2,3]triazolo[4,5-c]pyridine (207 mg) were combined with DMF (12.9 mL) to give a white suspension. N-ethyldiisopropylamine (587 mg) was added dropwise over a period of 2 minutes at room temperature. Then, HATU (638 mg) was added and the reaction mixture was stirred for 15 h at rt. The mixture was poured into ice/water and the aqueous phase was extracted two times with ethyl acetate. The combined organic layers were washed with brine, dried over $Na_2SO_4$, filtered and evaporated. The residue was once again evaporated with toluene. The crude material was purified by flash chromatography (silica gel, 20 g, 0% to 10% MeOH in $CH_2Cl_2$) to give a white foam (310 mg). MS: 389.3 $[M+H]^+$.

Step 2: 1,4,6,7-tetrahydrotriazolo[4,5-c]pyridin-5-yl(6,7,8,9-tetrahydro-5H-[1,2,4]triazolo[1,5-d][1,4]diazepin-2-yl)methanone hydrochloride

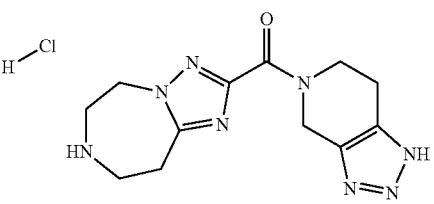 [SMILES: Cl ; O=C(c1nc2n(n1)CCNCC2)N1CCc2[nH]nnc2C1]

In a 20 mL round-bottom flask, tert-butyl 2-(4,5,6,7-tetrahydro-1H-[1,2,3]triazolo[4,5-c]pyridine-5-carbonyl)-8,9-dihydro-5H-[1,2,4]triazolo[1,5-d][1,4]diazepine-7(6H)-carboxylate (230 mg) and 5N HCl in 2-propanol (5 mL) were combined to give a white suspension. The reaction mixture was heated to 50° C. with stirring for 2 hours. The reaction mixture was then cooled and concentrated in vacuo to give a crude salt (190 mg) which was used without further purification. MS: 289.1 $[M+H]^+$.

Intermediate 11

3-[3-chloro-4-(trifluoromethoxy)phenyl]propanoic acid

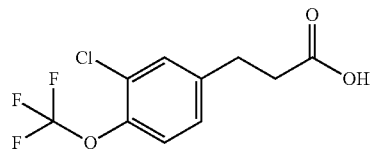 [SMILES: O=C(O)CCc1ccc(OC(F)(F)F)c(Cl)c1]

Step 1: (E)-3-[3-chloro-4-(trifluoromethoxy)phenyl]prop-2-enoic acid

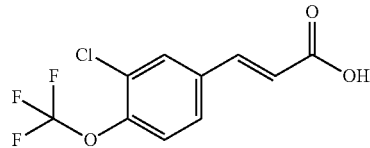 [SMILES: O=C(O)/C=C/c1ccc(OC(F)(F)F)c(Cl)c1]

In a 20 mL round-bottom flask, 3-chloro-4-(trifluoromethoxy)benzaldehyde (CAS: 83279-39-4, 500 mg), malonic acid (510 mg) and piperidine (22.0 µL) were combined with pyridine (3.0 mL) to give a colorless solution. The mixture was then heated to reflux for 5 h. The reaction mixture was cooled, poured into ice/water and acidified with 2N HCl. The aqueous phase was extracted 2 times with ethyl acetate and the combined organic layers were washed with brine, dried over $Na_2SO_4$, filtered and

Step 2: 3-[3-chloro-4-(trifluoromethoxy)phenyl] propanoic acid

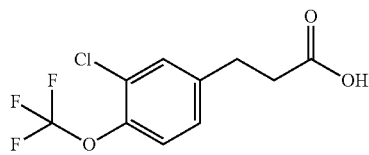

In a 50 mL three-neck flask, (E)-3-[3-chloro-4-(trifluoromethoxy)phenyl]prop-2-enoic acid (300 mg) was combined with ethyl acetate (10 mL) to give a colorless solution. Palladium on charcoal (10% Pd, 40 mg) was added and the mixture was then hydrogenated for 30 min, where TLC analysis showed no residual starting material. The reaction mixture was filtered through celite and was then concentrated in vacuo to give a light yellow solid (300 mg) which was used without further purification. MS: 267.3 [M−H]⁻.

Intermediate 12

2-Cyclopropyl-6-(oxan-4-ylmethoxy)pyridine-4-carboxylic acid

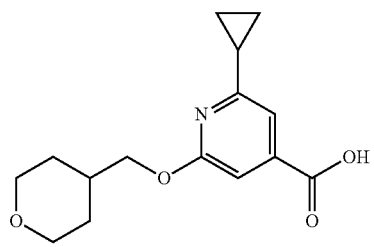 [SMILES: O=C(O)c1cc(OCC2CCOCC2)nc(C2CC2)c1]

Step 1: Methyl 6-cyclopropyl-2-oxo-1,2-dihydropyridine-4-carboxylate

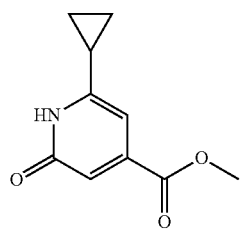

A suspension of 6-cyclopropyl-2-oxo-1,2-dihydropyridine-4-carboxylic acid (CAS: 150190-28-6; 400 mg) in methanol (4 mL) and sulfuric acid (12 µL) was heated at 70° C. for 48 h. The mixture was then concentrated in vacuo. The residue was suspended in dichloromethane (10 mL), then insoluble material was removed by filtration and the filtrate was evaporated to produce the title compound (427 mg) as a light brown semisolid. MS: 194.1 [M+H]⁺.

Step 2: Methyl 2-cyclopropyl-6-(oxan-4-ylmethoxy)pyridine-4-carboxylate

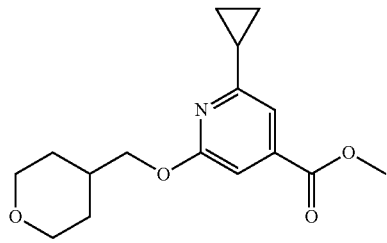 [SMILES: COC(=O)c1cc(OCC2CCOCC2)nc(C2CC2)c1]

To suspension of methyl 6-cyclopropyl-2-oxo-1,2-dihydropyridine-4-carboxylate (212 mg) in acetonitrile (5 mL) were added potassium carbonate (455 mg) and 4-(iodomethyl)tetrahydro-2H-pyran (CAS: 101691-94-5; 744 mg) with stirring. The reaction mixture was heated at 80° C. for 16 h and was then evaporated in vacuo. The residue was purified by flash chromatography (silica gel; heptane-ethyl acetate gradient) to produce the title compound as a colorless oil (188 mg). MS: 292.2 [M+H]⁺.

Step 3: 2-cyclopropyl-6-(oxan-4-ylmethoxy)pyridine-4-carboxylic acid

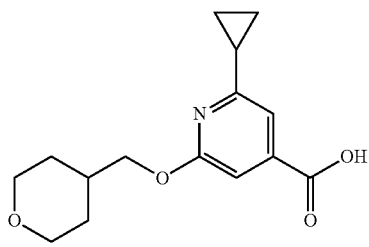 [SMILES: O=C(O)c1cc(OCC2CCOCC2)nc(C2CC2)c1]

To a solution of methyl 2-cyclopropyl-6-(oxan-4-ylmethoxy)pyridine-4-carboxylate (184 mg) in tetrahydrofuran (2 mL) and water (2 mL) was added lithium hydroxide monohydrate (53.0 mg, 1.26 mmol) and the resulting mixture was stirred at room temperature for 16 h. The mixture was partially evaporated in order to remove the tetrahydrofuran. The aqueous phase was partitioned between 1 M aq. hydrochloric acid solution and ethyl acetate. The layers were separated and the organic layer was washed with brine, dried over magnesium sulfate, filtered and evaporated to give the title compound as a colorless oil (218 mg). MS: 276.1 [M−H]⁻.

Intermediate 13

(E)-3-[4-(difluoromethoxy)-3-fluoro-phenyl]prop-2-enoic acid

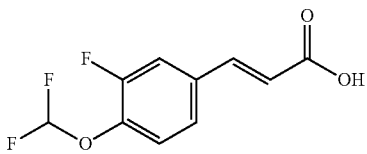 [SMILES: O=C(O)/C=C/c1ccc(OC(F)F)c(F)c1]

This material was made in analogy to Intermediate 11, Step 1 from 4-(difluoromethoxy)-3-fluorobenzaldehyde (CAS: 1214379-56-2, 1.54 g). MS: 233.1 [M+H]⁺.

Intermediate 14

6,7,8,9-tetrahydro-5H-imidazo[1,2-d][1,4]diazepin-2-yl(1,4,6,7-tetrahydrotriazolo[4,5-c]pyridin-5-yl)methanone

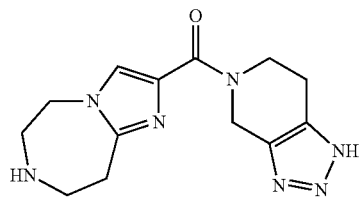 [SMILES: O=C(c1cn2c(n1)CCNCC2)N1CCc2[nH]nnc2C1]

This material was made in analogy to Example 3, Step 1, by hydrogenation of benzyl 2-(1,4,6,7-tetrahydrotriazolo[4,5-c]pyridine-5-carbonyl)-5,6,8,9-tetrahydroimidazo[1,2-d][1,4]diazepine-7-carboxylate (obtained in Example 2) to give the title compound 6,7,8,9-tetrahydro-5H-imidazo[1,2-d][1,4]diazepin-2-yl(1,4,6,7-tetrahydrotriazolo[4,5-c]pyridin-5-yl)methanone as a colorless powder. MS: 288.2 [M+H]⁺.

Intermediate 15

(3aR,7aR)-5-(6,7,8,9-Tetrahydro-5H-[1,2,4]triazolo[1,5-d][1,4]diazepine-2-carbonyl)hexahydro-[1,3]oxazolo[5,4-c]pyridin-2(1H)-one 2,2,2-trifluoroacetate

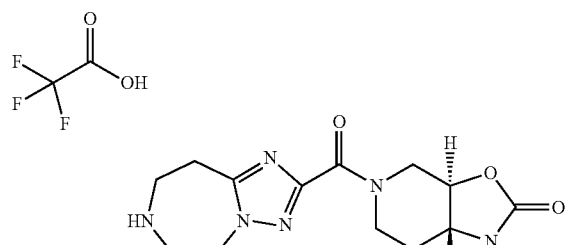

Step 1: tert-Butyl (3aR,7aR)-2-oxo-1,3a,4,6,7,7a-hexahydro-[1,3]oxazolo[5,4-c]pyridine-5-carboxylate

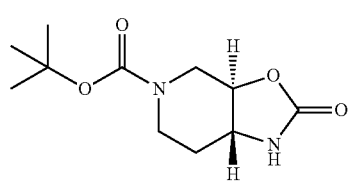 [SMILES: CC(C)(C)OC(=O)N1CC[C@H]2NC(=O)O[C@@H]2C1]

To a solution of (3R,4R)-tert-butyl 4-amino-3-hydroxypiperidine-1-carboxylate (CAS: 1007596-95-3, 510 mg) in DMF (8.0 mL) was added imidazole (161 mg) and then 1,1'-carbonyldiimidazole (382 mg) at room temperature under an argon atmosphere. The mixture was stirred at room temperature for 18 hours. Then, the reaction mixture was poured into ice/water and the aqueous layer was extracted twice with ethyl acetate. The organic layers were washed once with brine, dried over Na₂SO₄, filtered and evaporated. The residue was once again evaporated with toluene. The crude material was purified by flash chromatography (silica gel, 20 g cartridge, 0% to 5% methanol in dichloromethane) to provide the title compound as a white solid (460 mg). MS: 187.0 [M-56 (isobutylene)+H]⁺.

Step 2: (3aR,7aR)-3a,4,5,6,7,7a-hexahydro-1H-[1,3]oxazolo[5,4-c]pyridin-2-one hydrochloride

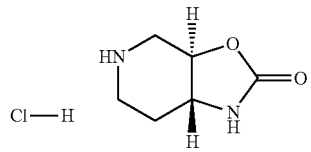

tert-Butyl (3aR,7aR)-2-oxo-1,3a,4,6,7,7a-hexahydro-[1,3]oxazolo[5,4-c]pyridine-5-carboxylate (458 mg) was combined with hydrochloric acid (approx. 5M-6M in isopropanol, 6.87 mL) and the mixture was stirred at room temperature for 19 hours. The reaction mixture was then directly evaporated to dryness. The white residue was combined with ethyl acetate (8 mL) and the suspension was stirred at room temperature for 1 hour. The colorless solid was isolated by filtration, washed with ethyl acetate and dried at high vacuum to provide the title compound (279 mg). MS: 143.0 [M+H]⁺ (free base).

Step 3: tert-Butyl 2-[(3aR,7aR)-2-oxo-1,3a,4,6,7,7a-hexahydro-[1,3]oxazolo[5,4-c]pyridine-5-carbonyl]-5,6,8,9-tetrahydro-[1,2,4]triazolo[1,5-d][1,4]diazepine-7-carboxylate

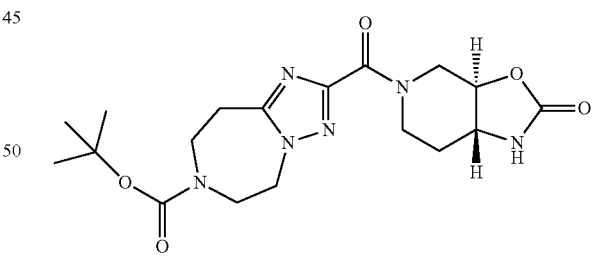

In a 50 mL round-bottom flask, (3aR,7aR)-3a,4,5,6,7,7a-hexahydro-1H-[1,3]oxazolo[5,4-c]pyridin-2-one hydrochloride (225 mg), 4-methylmorpholine (382 mg) and 4,5,7,8-tetrahydro-1,3,3a,6-tetraaza-azulene-2,6-dicarboxylic acid 6-tert-butyl ester (Intermediate 2, 391 mg) were combined with DMF (10.0 mL) to give a light yellow solution. 1-(3-Dimethylaminopropyl)-3-ethylcarbodiimide hydrochloride (483 mg) and 1-hydroxybenzotriazole hydrate (340 mg) were added and the reaction mixture was stirred for 16 hours at room temperature. The mixture was poured into ice/water and was extracted twice with ethyl acetate. The combined organic layers were washed with brine, dried over Na₂SO₄, filtered and evaporated. The residue was once again evaporated with toluene. The crude material was purified by flash chromatography (silica gel, 50 g cartridge, 0% to 10% methanol in dichloromethane) to provide the title compound as a colorless solid (491 mg). MS: 351.2 [M-56 (isobutylene)+H]⁺.

Step 4: (3aR,7aR)-5-(6,7,8,9-tetrahydro-5H-[1,2,4]triazolo[1,5-d][1,4]diazepine-2-carbonyl)hexahydro-[1,3]oxazolo[5,4-c]pyridin-2(1H)-one 2,2,2-trifluoroacetate

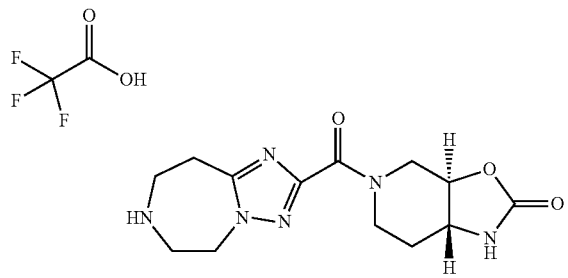 [SMILES: O=C(O)C(F)(F)F ; O=C1N[C@@H]2CCN(C(=O)c3nc4n(n3)CCNCC4)C[C@H]2O1]

tert-Butyl 2-[(3aR,7aR)-2-oxo-1,3a,4,6,7,7a-hexahydro-[1,3]oxazolo[5,4-c]pyridine-5-carbonyl]-5,6,8,9-tetrahydro-[1,2,4]triazolo[1,5-d][1,4]diazepine-7-carboxylate (50 mg) was dissolved in dichloromethane (5.0 mL) at room temperature under an argon atmosphere. Then, 2,2,2-trifluoroacetic acid (140 mg) was added dropwise over a period of 5 minutes and the mixture was stirred at room temperature for 3 hours. More 2,2,2-trifluoroacetic acid (42.1 mg) was slowly added and stirring was continued at room temperature for another 17 hours. Then, the solvent was removed by evaporation and residual TFA was removed by addition and evaporation of toluene. Following evaporation, the residue was dried at high vacuum to provide a light yellow gum (68 mg) that was used without further purification. MS: 307.2 [M+H]⁺ (free base).

EXAMPLES

Example 1

Benzyl 2-(1,4,6,7-tetrahydrotriazolo[4,5-c]pyridine-5-carbonyl)-4,5,7,8-tetrahydropyrazolo[1,5-d][1,4]diazepine-6-carboxylate

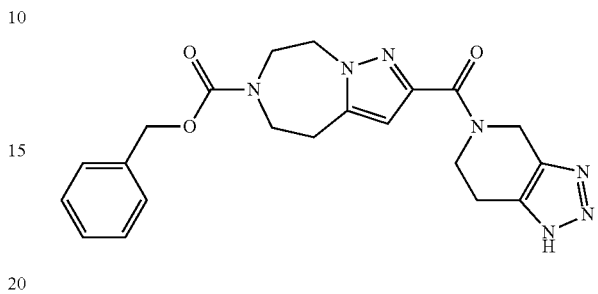

4-Methylmorpholine (1.56 g) was added drop wise over a period of 5 minutes to a suspension of 6-(benzyloxycarbonyl)-5,6,7,8-tetrahydro-4H-pyrazolo[1,5-d][1,4]diazepine-2-carboxylic acid (Intermediate 1, 1.62 g) and 4,5,6,7-tetrahydro-1H-[1,2,3]triazolo[4,5-c]pyridine (702 mg, [CAS: 706757-05-3]) in dimethylformamide (20 mL) at room temperature under an argon atmosphere. Then, HATU (2.17 g) was added in four portions. The mixture was stirred at room temperature for 17 hours. The reaction mixture was poured into ice/water. The aqueous phase was then extracted two times with ethyl acetate. The combined organic layers were washed with brine, dried over Na₂SO₄, filtered and evaporated. The residue was once again evaporated with toluene. The crude material was purified by flash chromatography (silica gel, 0% to 100% ethyl acetate in heptane and then CH₂Cl₂/MeOH=96/4) to give the title compound as a off-white foam (1.40 g, 62%). MS (m/e): 422.6 [M+H⁺].

The following Example 2 was synthesized from the suitable building block/intermediate in analogy to Example 1:

| Ex. | Systematic Name | Building block/ intermediate | MS, m/e |
|---|---|---|---|
| 2 | benzyl 2-(1,4,6,7-tetrahydrotriazolo[4,5-c]pyridine-5-carbonyl)-5,6,8,9-tetrahydroimidazo[1,2-d][1,4]diazepine-7-carboxylate | Intermediate 3 | 422.2 [M + H]⁺ |

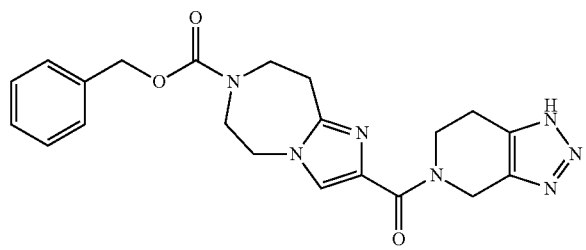

Example 3

[3-Fluoro-4-(trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate

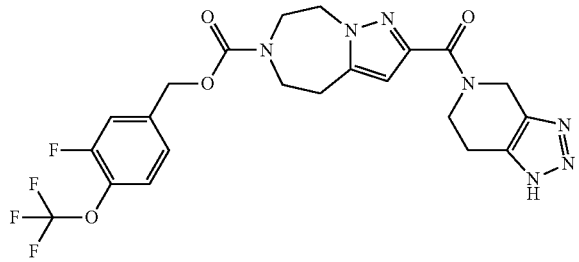 [SMILES: O=C(OCc1ccc(OC(F)(F)F)c(F)c1)N1CCc2cc(C(=O)N3CCc4[nH]nnc4C3)nn2CC1]

Step 1: 5,6,7,8-Tetrahydro-4H-pyrazolo[1,5-d][1,4]diazepin-2-yl(1,4,6,7-tetrahydrotriazolo[4,5-c]pyridin-5-yl)methanone

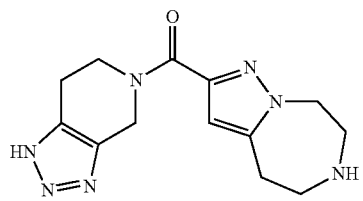 [SMILES: O=C(c1cc2n(n1)CCNCC2)N1CCc2[nH]nnc2C1]

Benzyl 2-(4,5,6,7-tetrahydro-1H-[1,2,3]triazol[4,5-c]pyridine-5-carbonyl)-7,8-dihydro-4H-pyrazolo[1,5-d][1,4]diazepine-6(5H)-carboxylate (1.40 g, obtained in Example 1) was dissolved in methanol (10 mL) to give a colorless solution. Palladium on activated charcoal (140 mg, 10% Pd) was added and an atmosphere of hydrogen was introduced at rt. The mixture was stirred under hydrogen for 16 hours. The reaction mixture was filtered over dicalite speed plus (Acros Organics) and the solvent was evaporated to dryness to give the title compound as a colorless oil (910 mg, 94%). MS (m/e): 288.2 [M+H$^+$].

Step 2: [3-Fluoro-4-(trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate

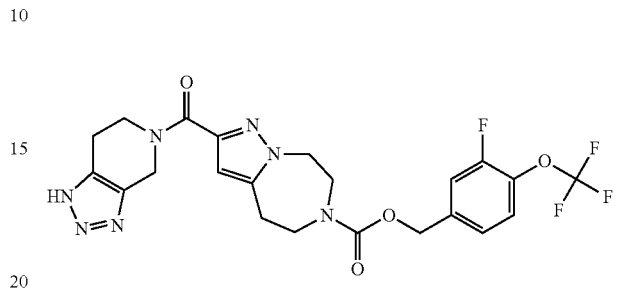

Triethylamine (31.7 mg) was added to a solution of (3-fluoro-4-(trifluoromethoxy)phenyl)methanol (CAS: 886498-99-3, 98.7 mg) in acetonitrile (8.0 mL) at room temperature under an argon atmosphere. Then, N,N'-disuccinimidyl carbonate (120 mg) was added and the colorless solution was stirred at room temperature for 3 hours to give the activated alcohol. (6,7-dihydro-1H-[1,2,3]triazolo[4,5-c]pyridin-5(4H)-yl)(5,6,7,8-tetrahydro-4H-pyrazolo[1,5-d][1,4]diazepin-2-yl)methanone (90 mg) and triethylamine (95.1 mg) were added to the colorless solution and the mixture was stirred at room temperature for 18 h. The reaction mixture was poured into ice/water and the aqueous phase was extracted two times with ethyl acetate. The combined organic layers were washed with brine, dried over Na$_2$SO$_4$, filtered and evaporated. Toluene was added and the solvent was once again evaporated. The crude material was purified by flash chromatography (silica gel, gradient of ethyl acetate in heptane) to give the title compound as a white solid (53 mg, 32%). MS (m/e): 524.6 [M+H]$^+$.

The following Examples 4-13 were synthesized from the suitable building block and the corresponding substituted benzyl alcohol in analogy to Example 2, Step 2:

| Ex. | Systematic Name | Building block/intermediate | Benzyl alcohol | MS, m/e |
|---|---|---|---|---|
| 4 | 2-Fluoro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | (2-fluoro-4-(trifluoromethoxy)-phenyl)-methanol CAS: 1240257-07-1 | 524.5 [M + H]$^+$ |

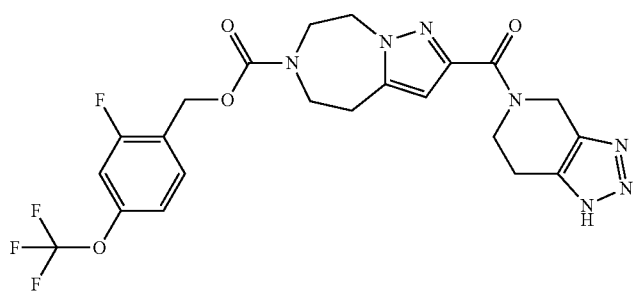 [SMILES: O=C(CCc1ccc(OC(F)(F)F)cc1)N1CCc2cc(C(=O)N3CCc4[nH]nnc4C3)nn2CC1]

-continued

| Ex. | Systematic Name | Building block/intermediate | Benzyl alcohol | MS, m/e |
|---|---|---|---|---|
| 5 | [4-(Trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate | Intermediate 9 | (4-trifluoromethoxy-phenyl)methanol CAS: 1736-74-9 | 506.3 [M + H]+ |
| 6 | 4-Cyanobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | 4-(hydroxymethyl)-benzonitrile CAS: 874-89-5 | 447.2 [M + H]+ |
| 7 | 4-Cyano-3-fluorobenzyl 2-(4,5,6,-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | 2-Fluoro-4-(hydroxymethyl)-benzonitrile CAS: 222978-02-1 | 465.2 [M + H]+ |

-continued

| Ex. | Systematic Name | Building block/ intermediate | Benzyl alcohol | MS, m/e |
|---|---|---|---|---|
| 8 | 4-Cyano-2-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | 3-Fluoro-4-(hydroxymethyl)-benzonitrile CAS: 219873-06-0 | 465.3 [M + H]⁺ |
| 9 | (4-Cyano-2-propan-2-ylphenyl)methyl 2-(1,4,6,7-tetrahydrotriazolo[4,5-c]pyridine-5-carbonyl)-4,5,7,8-tetrahydropyrazolo[1,5-d][1,4]diazepine-6-carboxylate | Intermediate 9 | 4-(hydroxymethyl)-3-isopropyl-benzonitrile (Intermediate 4) | 489.4 [M + H]⁺ |
| 10 | [4-Cyano-2-(2,2-dimethylpropanoylamino)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate | Intermediate 9 | N-[5-cyano-2-(hydroxymethyl)-phenyl]-2,2-dimethylpropan-amide (Intermediate 5) | 546.4 [M + H]⁺ |

| Ex. | Systematic Name | Building block/ intermediate | Benzyl alcohol | MS, m/e |
|---|---|---|---|---|
| 11 | [4-(Trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate | Intermediate 2 | (4-trifluoromethoxyphenyl)methanol CAS: 1736-74-9 | 507.3 [M + H]⁺ |
| 12 | [4-Cyano-2-(2,2-dimethylpropanoylamino)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate | Intermediate 2 | N-[5-cyano-2-(hydroxymethyl)phenyl]-2,2-dimethylpropanamide (Intermediate 5) | 547.4 [M + H]⁺ |
| 13 | [4-(Trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate | Intermediate 3 | (4-trifluoromethoxyphenyl)methanol CAS: 1736-74-9 | 506.2 [M + H]⁺ |

Example 14

1-[2-(1,4,6,7-tetrahydrotriazolo[4,5-c]pyridine-5-carbonyl)-4,5,7,8-tetrahydropyrazolo[1,5-d][1,4]diazepin-6-yl]-3-[4-(trifluoromethoxy)phenyl]propan-1-one

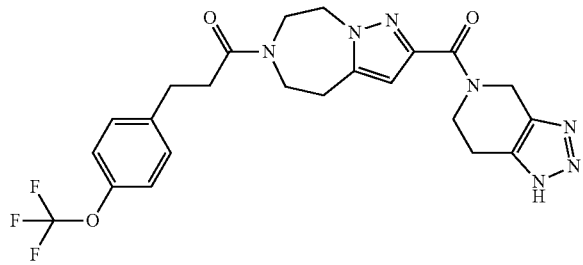

4-Methylmorpholine (84.5 mg) was added drop wise over a period of 5 minutes to a suspension of (6,7-dihydro-1H-[1,2,3]triazolo[4,5-c]pyridin-5(4H)-yl)(5,6,7,8-tetrahydro-4H-pyrazolo[1,5-d][1,4]diazepin-2-yl)methanone (Intermediate 9, 80 mg) and 3-(4-(trifluoromethoxy)phenyl)propanoic acid (CAS: 886499-74-7; 71.7 mg) in dimethylformamide (4.0 mL) at room temperature under an argon atmosphere. The mixture was cooled down to 0° C. and HATU (117 mg) was added. The mixture was warmed up to room temperature for 17 h. The reaction mixture was poured into ice/water and the aqueous phase was then extracted two times with ethyl acetate. The combined organic layers were washed with brine, dried over $Na_2SO_4$, filtered and evaporated. Toluene was added and the mixture was once again evaporated. The crude material was purified by flash chromatography (silica gel, gradient of ethyl acetate in heptane) to give the title compound as a white solid (13 mg, 10%). MS (m/e): 504.6 [M+H]$^+$ The following Examples 15-17 were synthesized in analogy to Example 10 from Intermediate 9 and the corresponding substituted carboxylic acids:

| Ex. | Systematic Name | Building block | Carboxylic acid | MS, m/e |
|---|---|---|---|---|
| 15 | 3-Cyclopropyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile | Intermediate 9 | 2-(4-cyano-2-cyclopropyl-phenoxy)acetic acid (Intermediate 6) | 487.4 [M + H]$^+$ |

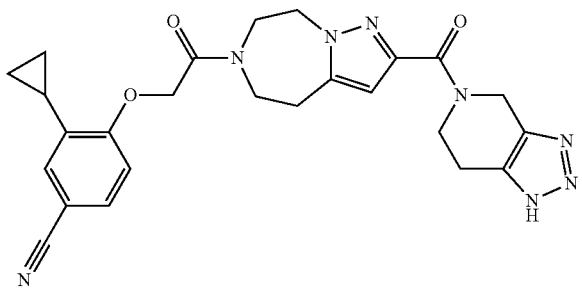

| 16 | 3-Ethyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile | Intermediate 9 | 2-(4-cyano-2-ehtylphenoxy)-acetic acid (Intermediate 7) | 475.4 [M + H]$^+$ |

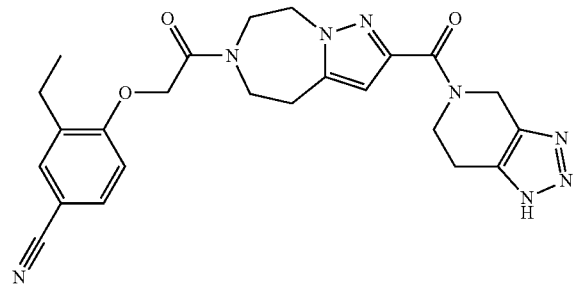

| Ex. | Systematic Name | Building block | Carboxylic acid | MS, m/e |
|---|---|---|---|---|
| 17 | 3-tert-Butyl-4-[2-oxo-2-[2-(1,4,6,7-tetrahydrotriazolo[4,5-c]pyridine-5-carbonyl)-4,5,7,8-tetrahydropyrazolo[1,5-d][1,4]diazepin-6-yl]ethoxy]benzonitrile | Intermediate 9 | 2-(2-tert-butyl-4-cyanophenoxy)-acetic acid (Intermediate 8) | 503.4 [M + H]+ |
| 18 | 3-[3-fluoro-4-(trifluoromethoxy)phenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one | Intermediate 9 | 3-[3-fluoro-4-(trifluoromethoxy)phenyl]propanoic acid CAS: 1261616-38-9 Made according to WO2014048865 | 522.2 [M + H]+ |
| 19 | 3-(4-methoxyphenyl)-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one | Intermediate 9 | 3-(4-methoxyphenyl)propanoic acid CAS: 1929-29-9 | 450.3 [M + H]+ |

-continued

| Ex. | Systematic Name | Building block | Carboxylic acid | MS, m/e |
|---|---|---|---|---|
| 20 | 1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]-3-[4-(trifluoromethoxy)phenyl]propan-1-one | Intermediate 10 | 3-(4-(trifluoromethoxy)phenyl)propanoic acid CAS: 886499-74-7 | 505.2 [M + H]$^+$ |
| 21 | 3-[3-fluoro-4-(trifluoromethoxy)phenyl]-1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]propan-1-one | Intermediate 10 | 3-[3-fluoro-4-(trifluoromethoxy)phenyl]propanoic acid CAS: 1261616-38-9 Made according to WO2014048865 | 523.3 [M + H]$^+$ |
| 22 | 3-[3-chloro-4-(trifluoromethoxy)phenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one | Intermediate 9 | 3-[3-chloro-4-(trifluoromethoxy)phenyl]propanoic acid CAS: 1261873-29-3 Intermediate 11 | 538.3 [M + H]$^+$ |

| Ex. | Systematic Name | Building block | Carboxylic acid | MS, m/e |
|---|---|---|---|---|
| 23 | 3-[3-chloro-4-(trifluoromethoxy)phenyl]-1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]propan-1-one | Intermediate 10 | 3-[3-chloro-4-(trifluoromethoxy)phenyl]propanoic acid CAS: 1261873-29-3 Intermediate 11 | 539.3 [M + H]+ |
| 24 | (6-(2-cyclopropyl-6-((tetrahydro-2H-pyran-4-yl)methoxy)isonicotinoyl)-5,6,7,8-tetrahydro-4H-pyrazolo[1,5-d][1,4]diazepin-2-yl)(6,7-dihydro-1H-[1,2,3]triazolo[4,5-c]pyridin-5(4H)-yl)methanone | Intermediate 9 | Intermediate 12 | 547.3 [M + H]+ |
| 25 | (E)-3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]prop-2-en-1-one | Intermediate 9 | (E)-3-[4-(difluoromethoxy)-3-fluoro-phenyl]prop-2-enoic acid Intermediate 13 (CAS: 1262013-95-5) | 502.2 [M + H]+ |

Example 26

3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one

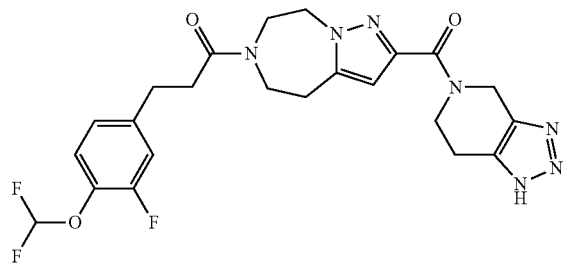 [SMILES: O=C(CCc1ccc(OC(F)F)c(F)c1)N1CCc2cc(C(=O)N3CCc4[nH]nnc4C3)nn2CC1]

In a 25 mL three-neck flask, (E)-3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]prop-2-en-1-one (Example 25, 35 mg) was combined with EtOH (5 mL) to give a colorless solution. The mixture was degassed and Pd/C (10% Pd, 20 mg) was added under nitrogen, followed by introduction of a hydrogen atmosphere. Then, the mixture was allowed to stir at room temperature over night. Hydrogen was then removed and the reaction mixture was filtered through celite. The filtrate was evaporated to give a crude material as a white foam. This residue was purified by flash chromatography (silica gel, 10 g, 0% to 50% MeOH in DCM) to give the title compound as a white foam (20 mg). MS: 504.2 [M+H]$^+$.

Example 27

4-methoxybenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate

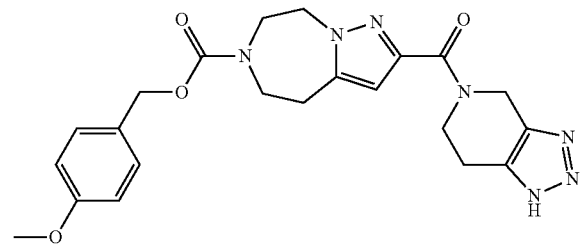 [SMILES: COc1ccc(COC(=O)N2CCc3cc(C(=O)N4CCc5[nH]nnc5C4)nn3CC2)cc1]

This material was made in analogy to Example 3, Step 2, from 5,6,7,8-tetrahydro-4H-pyrazolo[1,5-d][1,4]diazepin-2-yl(1,4,6,7-tetrahydrotriazolo[4,5-c]pyridin-5-yl)methanone (Intermediate 9) and (4-methoxyphenyl)methanol (CAS: 105-13-5). MS: 452.3 [M+H]$^+$.

The following Examples 28-43 were synthesized from the suitable building block and the corresponding substituted benzyl alcohol in analogy to Example 27:

| Ex. | Systematic Name | Building block/intermediate | Benzyl alcohol | MS, m/e |
|---|---|---|---|---|
| 28 | 4-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | (4-fluorophenyl)methanol CAS: 459-56-3 | 440.2 [M + H]$^+$ |

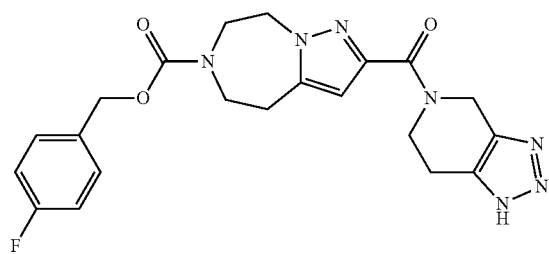

| Ex. | Systematic Name | Building block/ intermediate | Benzyl alcohol | MS, m/e |
|---|---|---|---|---|
| 29 | 3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | (3-fluorophenyl) methanol CAS: 456-47-3 | 440.3 [M + H]$^+$ |
| 30 | (3,4-difluorophenyl)methyl 2-(1,4,6,7-tetrahydrotriazolo[4,5-c]pyridine-5-carbonyl)-4,5,7,8-tetrahydropyrazolo[1,5-d][1,4]diazepine-6-carboxylate | Intermediate 9 | (3,4-difluorophenyl) methanol CAS: 85118-05-4 | 458.3 [M + H]$^+$ |
| 31 | 4-(difluoromethoxy)-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | [4-(difluoromethoxy)-3-fluoro-phenyl]methnaol CAS: 1242252-59-0 Made according to WO 2014048865 | 506.3 [M + H]$^+$ |

-continued

| Ex. | Systematic Name | Building block/intermediate | Benzyl alcohol | MS, m/e |
|---|---|---|---|---|
| 32 | 3-fluoro-4-methoxybenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | [3-fluoro-4-methoxy-phenyl]methanol CAS: 96047-32-4 | 470.3 [M + H]$^+$ |
| 33 | 4-methoxy-2-methylbenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | [4-(methoxy)-2-methyl-phenyl]methanol CAS: 52289-55-1 | 466.4 [M + H]$^+$ |
| 34 | 4-cyclopropylbenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | (4-cyclopropyl-phenyl)methanol CAS: 454678-87-6 | 462.4 [M + H]$^+$ |

| Ex. | Systematic Name | Building block/ intermediate | Benzyl alcohol | MS, m/e |
|---|---|---|---|---|
| 35 | [2-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate | Intermediate 10 | [2-fluoro-4-(trifluoromethoxy)phenyl]methanol CAS: 1240257-07-1 | 525.3 [M + H]$^+$ |
| 36 | [3-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate | Intermediate 10 | [3-fluoro-4-(trifluoromethoxy)phenyl]methanol CAS: 886498-99-3 | 525.2 [M + H]$^+$ |
| 37 | 3-chloro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | [3-chloro-4-(trifluoromethoxy)phenyl]methanol CAS: 56456-48-5 | 540.2 [M + H]$^+$ |

| Ex. | Systematic Name | Building block/ intermediate | Benzyl alcohol | MS, m/e |
|---|---|---|---|---|
| 38 | 2-methoxy-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | [2-methoxy-4-(trifluoromethoxy)phenyl]methanol CAS: 886500-30-7 | 536.2 [M + H]$^+$ |
| 39 | 2-methyl-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | [2-methyl-4-(trifluoromethoxy)phenyl]methanol CAS: 261951-94-4 | 520.2 [M + H]$^+$ |
| 40 | 4-(2,2,2-trifluoroethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate | Intermediate 9 | [4-(2,2,2-trifluoroethoxy)phenyl]methanol CAS: 1020949-12-5 | 520.2 [M + H]$^+$ |

| Ex. | Systematic Name | Building block/ intermediate | Benzyl alcohol | MS, m/e |
|---|---|---|---|---|
| 41 | [3-chloro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate | Intermediate 10 | [3-chloro-4-(trifluoromethoxy)phenyl]methanol CAS: 56456-48-5 | 541.3 [M + H]⁺ |
| 42 | [3-chloro-4-(trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate | Intermediate 14 | [3-chloro-4-(trifluoromethoxy)phenyl]methanol CAS: 56456-48-5 | 540.3 [M + H]⁺ |
| 43 | 3-fluoro-4-(trifluoromethoxy)benzyl 2-((3aR,7aR)-2-oxooctahydrooxazolo[5,4-c]pyridine-5-carbonyl)-8,9-dihydro-5H-[1,2,4]triazolo[1,5-d][1,4]diazepine-7(6H)-carboxylate | Intermediate 15 | [3-fluoro-4-(trifluoromethoxy)phenyl]methanol CAS: 886498-99-3 | 543.3 [M + H]⁺ |

The invention claimed is:

1. A compound of formula (I)

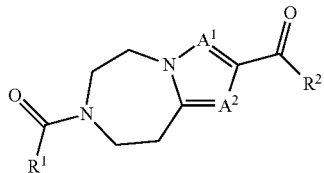

(I)

wherein

R¹ is substituted phenylalkyl, substituted phenoxyalkyl, substituted phenylalkoxy, or substituted phenylalkenyl, wherein substituted phenylalkyl, substituted phenoxyalkyl, substituted phenylalkoxy, and substituted phenylalkenyl are substituted with R³, R⁴ and R⁵;

A¹ is —N— or —CR⁷—;

A² is —N— or —CR⁸— and at least one of A¹ and A² is —N—;

R² is selected from the ring systems A, B, C, D, E, F, G, H, I, K and L

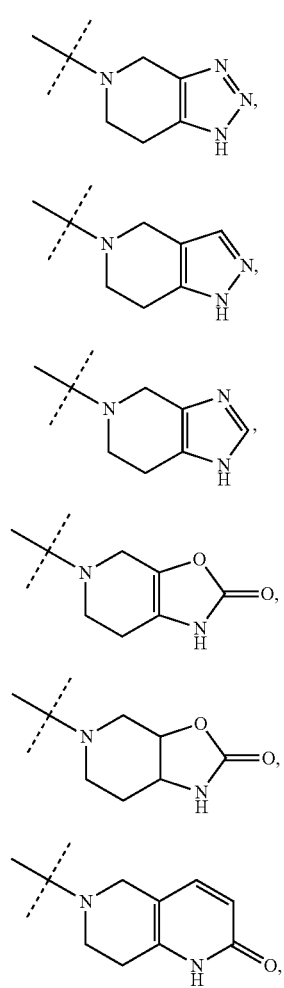

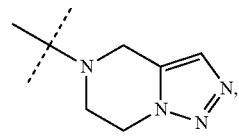

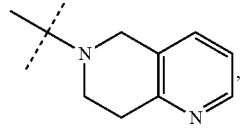

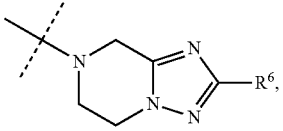

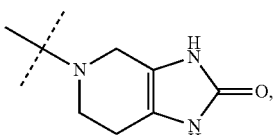

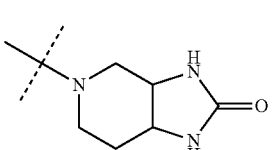

R³, R⁴ and R⁵ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, heterocycloalkylalkoxy, phenyl, substituted phenyl, pyridinyl, substituted pyridinyl, halogen, hydroxy, cyano, alkylsulfanyl, haloalkylsulfanyl, cycloalkylsulfanyl, alkylsulfanyl, haloalkylsulfinyl, cycloalkylsulfinyl, alkylsulfonyl, haloalkylsulfonyl, cycloalkylsulfonyl, alkylcarbonylamino, substituted aminosulfonyl, substituted amino and substituted aminoalkyl, wherein substituted aminosulfonyl, substituted amino and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl, and wherein substituted phenyl and substituted pyridinyl are optionally substituted with one to three substituents independently selected from alkyl, halogen, haloalkyl, alkoxy and haloalkoxy;

R⁶ is H, alkyl, haloalkyl or cycloalkyl; and

R⁷ and R⁸ are independently selected from H, alkyl, haloalkyl and cycloalkyl;

or a pharmaceutically acceptable salt thereof.

2. The compound of claim 1, wherein

R¹ is substituted phenylalkyl, substituted phenoxyalkyl, substituted phenylalkoxy, or substituted phenylalkenyl, wherein substituted phenylalkyl, substituted phenoxyalkyl, substituted phenylalkoxy, and substituted phenylalkenyl are substituted with R³, R⁴ and R⁵;

A¹ is —N— or —CR⁷—;

A² is —N— or —CR⁸— and at least one of A¹ and A² is —N—;

R² is selected from the ring systems A, B, C, D, E, F, G, H, I, K and L;

R³, R⁴ and R⁵ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, halogen, hydroxy, cyano, alkylsulfanyl, haloalkylsulfanyl, cycloalkylsulfanyl, alkylsulfinyl, haloalkylsulfinyl, cycloalkylsulfinyl, alkylsulfonyl, haloalkylsulfonyl, cycloalkylsulfonyl, alkylcarbonylamino, substituted aminosulfonyl, substituted amino and substituted aminoalkyl, wherein substituted aminosulfonyl, substituted amino and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl, and wherein substituted phenyl and substituted pyridinyl are optionally substituted with one to three substituents independently selected from alkyl, halogen, haloalkyl, alkoxy and haloalkoxy;

R⁶ is H, alkyl, haloalkyl or cycloalkyl; and

R⁷ and R⁸ are independently selected from H, alkyl, haloalkyl and cycloalkyl;

or a pharmaceutically acceptable salt thereof.

3. The compound of claim 1, or a pharmaceutically acceptable salt thereof, wherein R¹ is substituted phenylalkyl, substituted phenoxyalkyl or substituted phenylalkoxy, wherein substituted phenylalkyl, substituted phenoxyalkyl and substituted phenylalkoxy are substituted with R³, R⁴ and R⁵.

4. The compound of claim 1, or a pharmaceutically acceptable salt thereof, wherein R¹ is substituted phenoxyalkyl or substituted phenylalkoxy, wherein substituted phenoxyalkyl and substituted phenylalkoxy are substituted with R³, R⁴ and R⁵.

5. The compound of claim 1, or a pharmaceutically acceptable salt thereof, wherein R¹ is phenylalkoxy substituted with R³, R⁴ and R⁵.

6. The compound of claim 1, or a pharmaceutically acceptable salt thereof, wherein R² is selected from the ring systems A and E.

7. The compound of claim 1, or a pharmaceutically acceptable salt thereof, wherein R² is the ring system A.

8. The compound of claim 1, or a pharmaceutically acceptable salt thereof, wherein A¹ is —N— and A² is —N— or —CR⁸—.

9. The compound of claim 1, or a pharmaceutically acceptable salt thereof, wherein R³, R⁴ and R⁵ are independently selected from H, alkyl, cycloalkyl, heterocycloalkylalkoxy, haloalkoxy, halogen, cyano and alkylcarbonylamino.

10. The compound of claim 1, or a pharmaceutically acceptable salt thereof, wherein R³, R⁴ and R⁵ are independently selected from H, alkyl, cycloalkyl, haloalkoxy, halogen, cyano and alkylcarbonylamino.

11. The compound of claim 1, or a pharmaceutically acceptable salt thereof, wherein R³ is heterocycloalkylalkoxy, haloalkoxy or cyano.

12. The compound of claim 1, or a pharmaceutically acceptable salt thereof, wherein R³ is haloalkoxy or cyano.

13. The compound of claim 1, or a pharmaceutically acceptable salt thereof, wherein R⁴ is H, alkyl, cycloalkyl or halogen.

14. The compound of claim 1, or a pharmaceutically acceptable salt thereof, wherein R⁴ is H, alkyl or halogen.

15. The compound of claim 1, or a pharmaceutically acceptable salt thereof, wherein R⁵ is H.

16. The compound of claim 1, or a pharmaceutically acceptable salt thereof, wherein R⁷ is H.

17. The compound of claim 1, or a pharmaceutically acceptable salt thereof, wherein R⁸ is H.

18. The compound of claim 1, wherein
R¹ is substituted phenylalkoxy substituted with R³, R⁴ and R⁵;
A¹ is —N—;
A² is —N— or —CR⁸—;
R² is the ring system A;
R³ is haloalkoxy or cyano;
R⁴ is H or halogen;
R⁵ is H; and
R⁸ is H;
or a pharmaceutically acceptable salt thereof.

19. The compound of claim 1, selected from
Benzyl 2-(1,4,6,7-tetrahydrotriazolo[4,5-c]pyridine-5-carbonyl)-4,5,7,8-tetrahydropyrazolo[1,5-d][1,4]diazepine-6-carboxylate;
Benzyl 2-(1,4,6,7-tetrahydrotriazolo[4,5-c]pyridine-5-carbonyl)-5,6,8,9-tetrahydroimidazo[1,2-d][1,4]diazepine-7-carboxylate;
[3-Fluoro-4-(trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;
2-Fluoro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
[4-(Trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;
4-Cyanobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
4-Cyano-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
4-Cyano-2-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;
(4-Cyano-2-propan-2-ylphenyl)methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;
[4-Cyano-2-(2,2-dimethylpropanoylamino)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;
[4-(Trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;
[4-Cyano-2-(2,2-dimethylpropanoylamino)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;
[4-(Trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate;
1-[2-(1,4,6,7-Tetrahydrotriazolo[4,5-c]pyridine-5-carbonyl)-4,5,7,8-tetrahydropyrazolo[1,5-d][1,4]diazepin-6-yl]-3-[4-(trifluoromethoxy)phenyl]propan-1-one;

3-Cyclopropyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile;

3-Ethyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile;

3-tert-Butyl-4-[2-oxo-2-[2-(1,4,6,7-tetrahydrotriazolo[4,5-c]pyridine-5-carbonyl)-4,5,7,8-tetrahydropyrazolo[1,5-d][1,4]diazepin-6-yl]ethoxy]benzonitrile;

3-[3-fluoro-4-(trifluoromethoxy)phenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

3-(4-methoxyphenyl)-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]-3-[4-(trifluoromethoxy)phenyl]propan-1-one;

3-[3-fluoro-4-(trifluoromethoxy)phenyl]-1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]propan-1-one;

3-[3-chloro-4-(trifluoromethoxy)phenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

3-[3-chloro-4-(trifluoromethoxy)phenyl]-1-[2-(1,4,6,7-tetrahydrotriazolo[4,5-c]pyridine-5-carbonyl)-5,6,8,9-tetrahydro-[1,2,4]triazolo[1,5-d][1,4]diazepin-7-yl]propan-1-one;

(E)-3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]prop-2-en-1-one;

3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]propan-1-one;

4-methoxybenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

(3,4-difluorophenyl)methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

4-(difluoromethoxy)-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6-carboxylate;

3-fluoro-4-methoxybenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-methoxy-2-methylbenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-cyclopropylbenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[2-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[3-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

3-chloro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

2-methoxy-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

2-methyl-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-(2,2,2-trifluoroethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[3-chloro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[3-chloro-4-(trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate; and 3-fluoro-4-(trifluoromethoxy)benzyl 2-((3aR,7aR)-2-oxooctahydrooxazolo[5,4-c]pyridine-5-carbonyl)-8,9-dihydro-5H-[1,2,4]triazolo[1,5-d][1,4]diazepine-7(6H)-carboxylate;

or a pharmaceutically acceptable salt thereof.

20. A compound according to claim 1, selected from

Benzyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

Benzyl 2-(1,4,6,7-tetrahydrotriazolo[4,5-c]pyridine-5-carbonyl)-5,6,8,9-tetrahydroimidazo[1,2-d][1,4]diazepine-7-carboxylate;

[3-Fluoro-4-(trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

2-Fluoro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[4-(Trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

4-Cyanobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-Cyano-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

4-Cyano-2-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

(4-Cyano-2-propan-2-ylphenyl)methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

[4-Cyano-2-(2,2-dimethylpropanoylamino)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

[4-(Trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[4-Cyano-2-(2,2-dimethylpropanoylamino)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[4-(Trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate;

1-[2-(1,4,6,7-Tetrahydrotriazolo[4,5-c]pyridine-5-carbonyl)-4,5,7,8-tetrahydropyrazolo[1,5-d][1,4]diazepin-6-yl]-3-[4-(trifluoromethoxy)phenyl]propan-1-one;

3-Cyclopropyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile;

3-Ethyl-4-(2-oxo-2-(2-(4,5,6,7-tetrahydro-1H-[1,2,3]triazolo[4,5-c]pyridine-5-carbonyl)-7,8-dihydro-4H-pyrazolo[1,5-d][1,4]diazepin-6(5H)-yl)ethoxy)benzonitrile; and 3-tert-Butyl-4-[2-oxo-2-[2-(1,4,6,7-tetrahydrotriazolo[4,5-c]pyridine-5-carbonyl)-4,5,7,8-tetrahydropyrazolo[1,5-d][1,4]diazepin-6-yl]ethoxy]benzonitrile;

or a pharmaceutically acceptable salt thereof.

21. The compound of claim 1, selected from (E)-3-[4-(difluoromethoxy)-3-fluorophenyl]-1-[2-(1,4,6,7-tetrahydrotriazolo[4,5-c]pyridine-5-carbonyl)-4,5,7,8-tetrahydropyrazolo[1,5-d][1,4]diazepin-6-yl]prop-2-en-1-one;

4-(difluoromethoxy)-3-fluorobenzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[3-fluoro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

3-chloro-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

2-methyl-4-(trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[3-chloro-4-(trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate; and

[3-chloro-4-(trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate;

or a pharmaceutically acceptable salt thereof.

22. The compound of claim 1, selected from

3-Fluoro-4-(Trifluoromethoxy)benzyl 2-(4,5,6,7-tetrahydro-1H-[1,2,3]triazolo[4,5-c]pyridine-5-carbonyl)-7,8-dihydro-4H-pyrazolo[1,5-d][1,4]diazepine-6(5H)-carboxylate;

[4-(Trifluoromethoxy)phenyl]methyl 2-(1,4,6,7-tetrahydrotriazolo[4,5-c]pyridine-5-carbonyl)-4,5,7,8-tetrahydropyrazolo[1,5-d][1,4]diazepine-6-carboxylate;

[4-(Trifluoromethoxy)phenyl]methyl 2-(1,4,6,7-tetrahydrotriazolo[4,5-c]pyridine-5-carbonyl)-5,6,8,9-tetrahydro-[1,2,4]triazolo[1,5-d][1,4]diazepine-7-carboxylate;

[4-(Trifluoromethoxy)phenyl]methyl 2-(1,4,6,7-tetrahydrotriazolo[4,5-c]pyridine-5-carbonyl)-5,6,8,9-tetrahydroimidazo[1,2-d][1,4]diazepine-7-carboxylate; and 3-tert-Butyl-4-[2-oxo-2-[2-(1,4,6,7-tetrahydrotriazolo[4,5-c]pyridine-5-carbonyl)-4,5,7,8-tetrahydropyrazolo[1,5-d][1,4]diazepin-6-yl]ethoxy]benzonitrile;

or a pharmaceutically acceptable salt thereof.

23. A process to prepare a compound of claim 1, or a pharmaceutically acceptable salt thereof, comprising the reaction of a compound of formula (II) in the presence of a compound of formula (III), wherein $R^1$ is phenylalkoxy substituted with $R^3$, $R^4$ and $R^5$, and $R_A$ is phenylalkyl substituted with $R^3$, $R^4$ and $R^5$

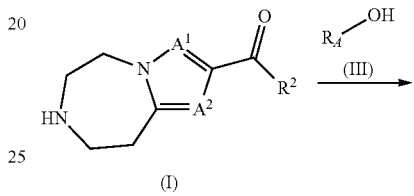

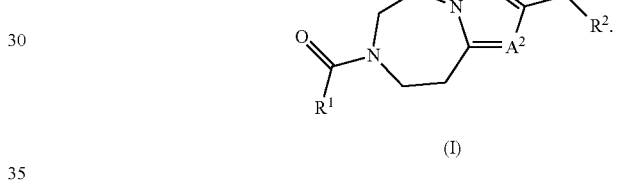

24. A process to prepare a compound of claim 1, or a pharmaceutically acceptable salt thereof, comprising the reaction of a compound of formula (II) in the presence of a compound of formula (IV), wherein $R^1$ is substituted phenylalkyl, substituted phenylalkyl, or substituted phenoxyalkyl, wherein substituted phenylalkenyl, substituted phenoxyalkyl, and substituted pheylalkenyl are substituted with $R^3$, $R^4$ and $R^5$

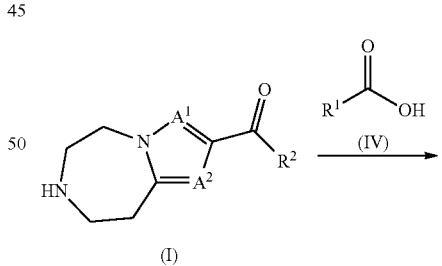

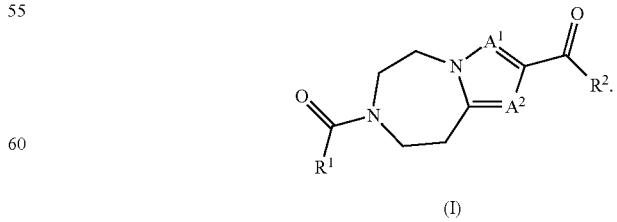

25. A pharmaceutical composition comprising a compound of claim 1, or a pharmaceutically acceptable salt thereof, and a therapeutically inert carrier.

26. A method for the treatment or prophylaxis of a condition selected from the group consisting of renal conditions, liver conditions, inflammatory conditions, conditions of the nervous system, fibrotic diseases and acute and chronic organ transplant rejection, which method comprises administering an effective amount of a compound of claim 1, or a pharmaceutically acceptable salt thereof.

* * * * *